(12) United States Patent
Biemans et al.

(10) Patent No.: US 8,846,080 B2
(45) Date of Patent: Sep. 30, 2014

(54) VACCINE

(75) Inventors: Ralph Leon Biemans, Rixensart (BE); Abdelatif Elouahabi, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 556 days.

(21) Appl. No.: 13/060,301

(22) PCT Filed: Aug. 26, 2009

(86) PCT No.: PCT/EP2009/060967
§ 371 (c)(1),
(2), (4) Date: Feb. 23, 2011

(87) PCT Pub. No.: WO2010/023216
PCT Pub. Date: Mar. 4, 2010

(65) Prior Publication Data
US 2011/0159081 A1    Jun. 30, 2011

Related U.S. Application Data

(60) Provisional application No. 61/092,582, filed on Aug. 28, 2008, provisional application No. 61/095,747, filed on Oct. 15, 2008, provisional application No. 61/165,688, filed on Apr. 1, 2009.

(51) Int. Cl.
*A61K 9/127* (2006.01)
*C07K 14/005* (2006.01)
*A61K 39/21* (2006.01)
*A61K 39/00* (2006.01)

(52) U.S. Cl.
CPC .............. *A61K 39/21* (2013.01); *C07K 14/005* (2013.01); *C12N 2710/10343* (2013.01); *C12N 2740/15071* (2013.01); *C12N 2740/15022* (2013.01); *A61K 2039/55566* (2013.01); *A61K 2039/55561* (2013.01); *A61K 2039/627* (2013.01); *A61K 2039/6018* (2013.01); *C12N 2740/15034* (2013.01)
USPC ....................................................... 424/450

(58) Field of Classification Search
CPC ............... A61K 2300/00; A61K 2039/55561; A61K 39/39; A61K 39/00; A61K 2039/6025; C12N 2310/321; C12N 15/117; C12N 2310/17
See application file for complete search history.

(56) References Cited

U.S. PATENT DOCUMENTS

| | | | | |
|---|---|---|---|---|
| 7,785,610 B2 * | 8/2010 | Fearon et al. | | 424/278.1 |
| 8,114,418 B2 * | 2/2012 | Fearon et al. | | 424/278.1 |
| 8,309,327 B2 * | 11/2012 | Biemans et al. | | 435/71.1 |
| 8,329,184 B2 * | 12/2012 | Biemans et al. | | 424/184.1 |
| 8,398,983 B2 * | 3/2013 | Biemans et al. | | 424/184.1 |

FOREIGN PATENT DOCUMENTS

| | | |
|---|---|---|
| WO | 03/000922 | 1/2003 |
| WO | WO 03/000922 A2 * | 1/2003 |
| WO | 2005/060377 | 7/2005 |
| WO | 2006/061253 | 6/2006 |
| WO | 2006/066003 | 6/2006 |

OTHER PUBLICATIONS

Muhs Andreas et al., Liposomal vaccines with conformation-specific amyloid peptide antigens define immune response and efficacy in APP transgenic mice, Proceedings of the National Academy of Sciences of USA, National Academy of Science, Washington DC, 104:23, 9810-9815 (Jun. 5, 2007).

Frisch Benoit et al., Synthetic peptide-based highly immunogenic liposomal constructs, Methods in Enzymology, 373:1, 51-73 (Jan. 1, 2003).

Esch M. B., et al., Detection of Cryptosporidium Parvum Using Oligonucleotides-Tagged Liposomes in a Competitive Assay Format, Analytical Chemistry, American Chemical Society, 73:13, 3162-3167 (Jul. 1, 2001).

Rule Geoffrey S. et al., Rapid method for visual identification of specific DNA sequences based on DNA-tagged liposomes, Clinical Chemistry, 42:8 part 1, 1206-1209 (1996).

Zhang Xue-Qing et al., A Comparative study of the antigen-specific immune response induced by co-delivery of CpG ODN and antigen using fusion molecules or biodegradable microparticles, Journal of Pharmaceutical Sciences, 96:12, 3283-3292 (Dec. 2007).

Li, W. M et al., Effective Induction of CD8+T-cell responses using CpG oligodeoxynucleotides and HER-2/neu-derived peptide co-encapsulated in liposomes, Vaccine, 21:23, 3319-3329 (Jul. 4, 2003).

* cited by examiner

*Primary Examiner* — Nita M Minnifield
(74) *Attorney, Agent, or Firm* — Michael M. Conger

(57) ABSTRACT

The present invention provides an immunogenic composition comprising at least one antigen delivery particle and at least one antigen, wherein the antigen and antigen delivery particle are linked using an intermediate linker.

32 Claims, 9 Drawing Sheets

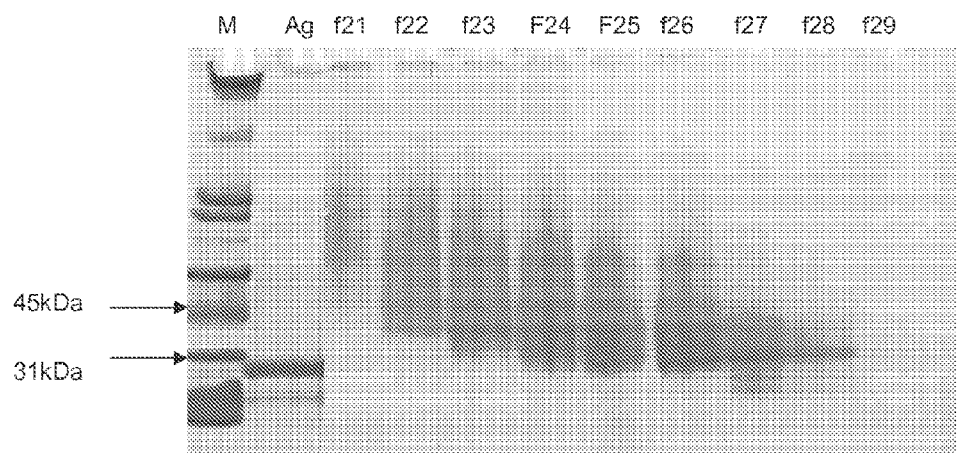
FIG. 1 - SDS-PAGE/Coomassie analysis of the different eluted fractions.

FIG. 2 - SDS-PAG/BET analysis of the different eluted fractions.
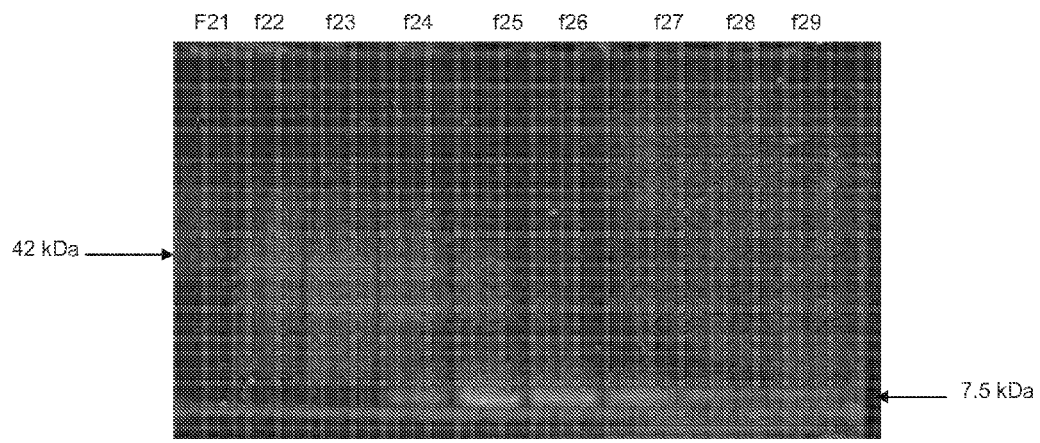

Figure 3A : SDS-PAGE analysis of pellet and supernatant after ultracentrifugation of the hybridization reaction mixture.
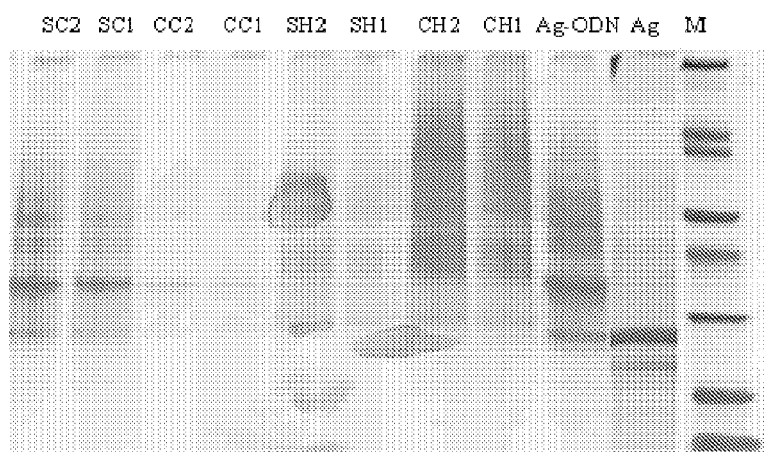
Legend:
SC = supernatant of control
CC = pellet of control
SH = supernatant of test
CH = pellet of test
Ag-ODN = p27-GpC conjugate
Ag = p27 alone
M = molecular weights
1 and 2 indicate double loading of the same samples.

Figure 3B : SDS-PAGE analysis of pellet and supernatant after ultracentrifugation of the hybridization reaction mixture.
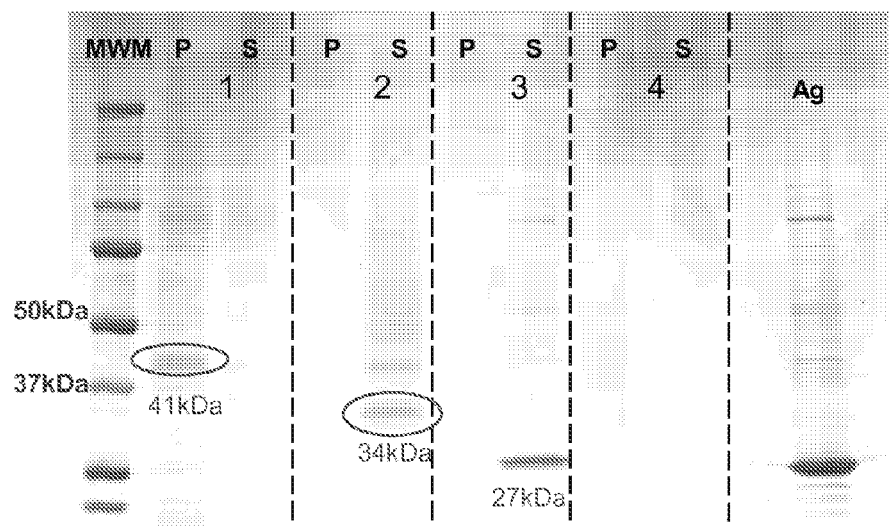
1: Hybrid p27-GpC-CpG-Lipo
2: p27-GpC / Lipo w/o CpG
3: p27
4: Liposomes w/o CpG
Ag: free Antigen as control
P: pellet
S: supernatant
MWM: molecular weight markers

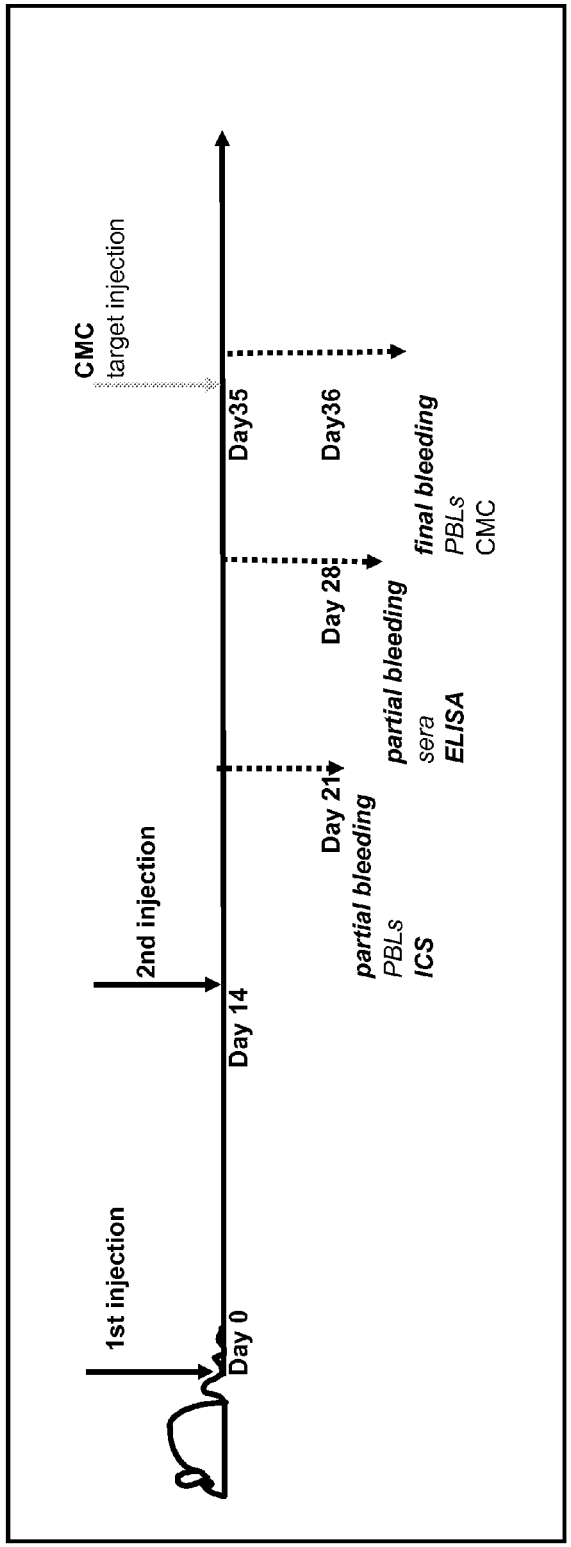
Figure 4 - study design

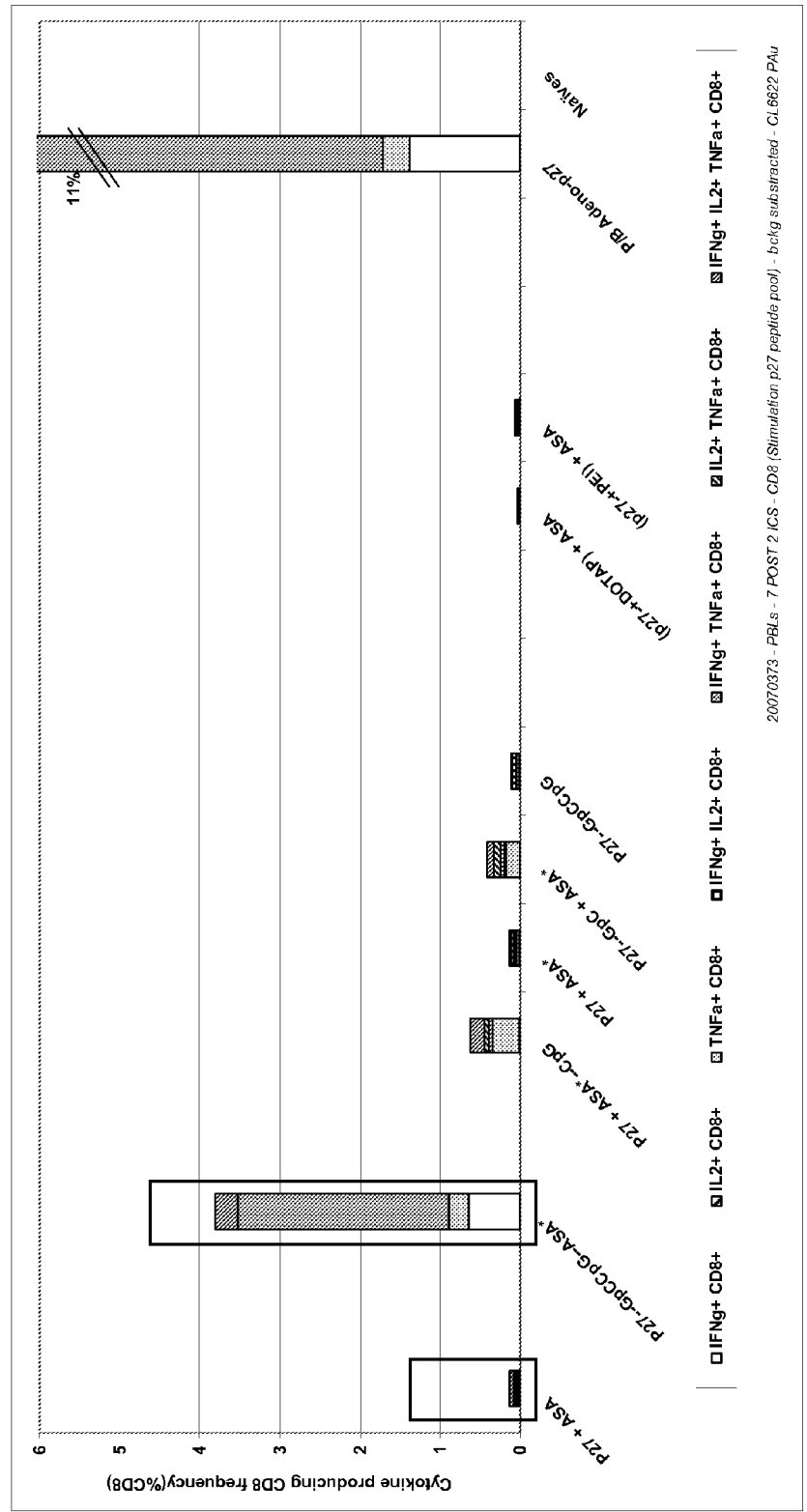

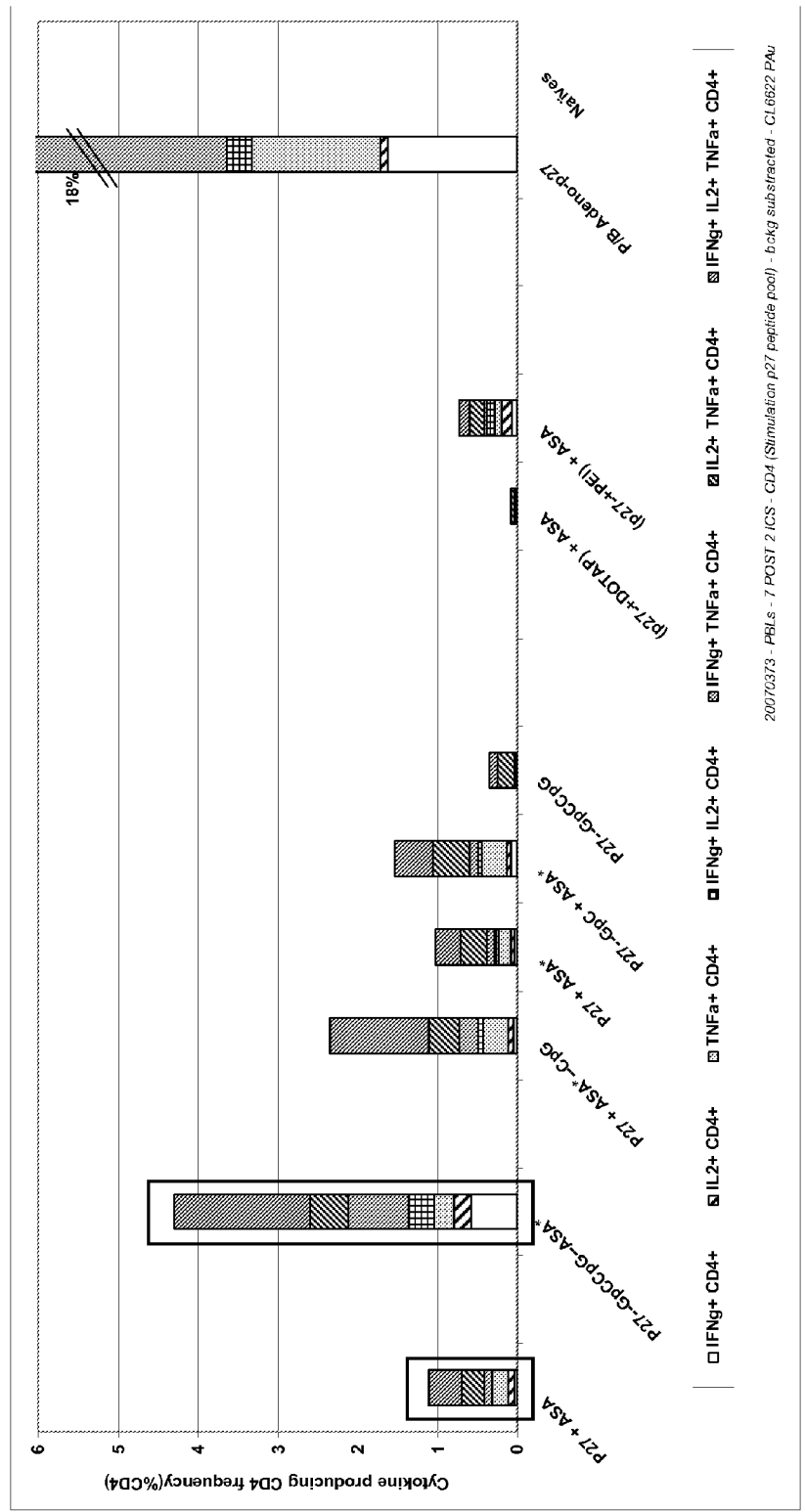

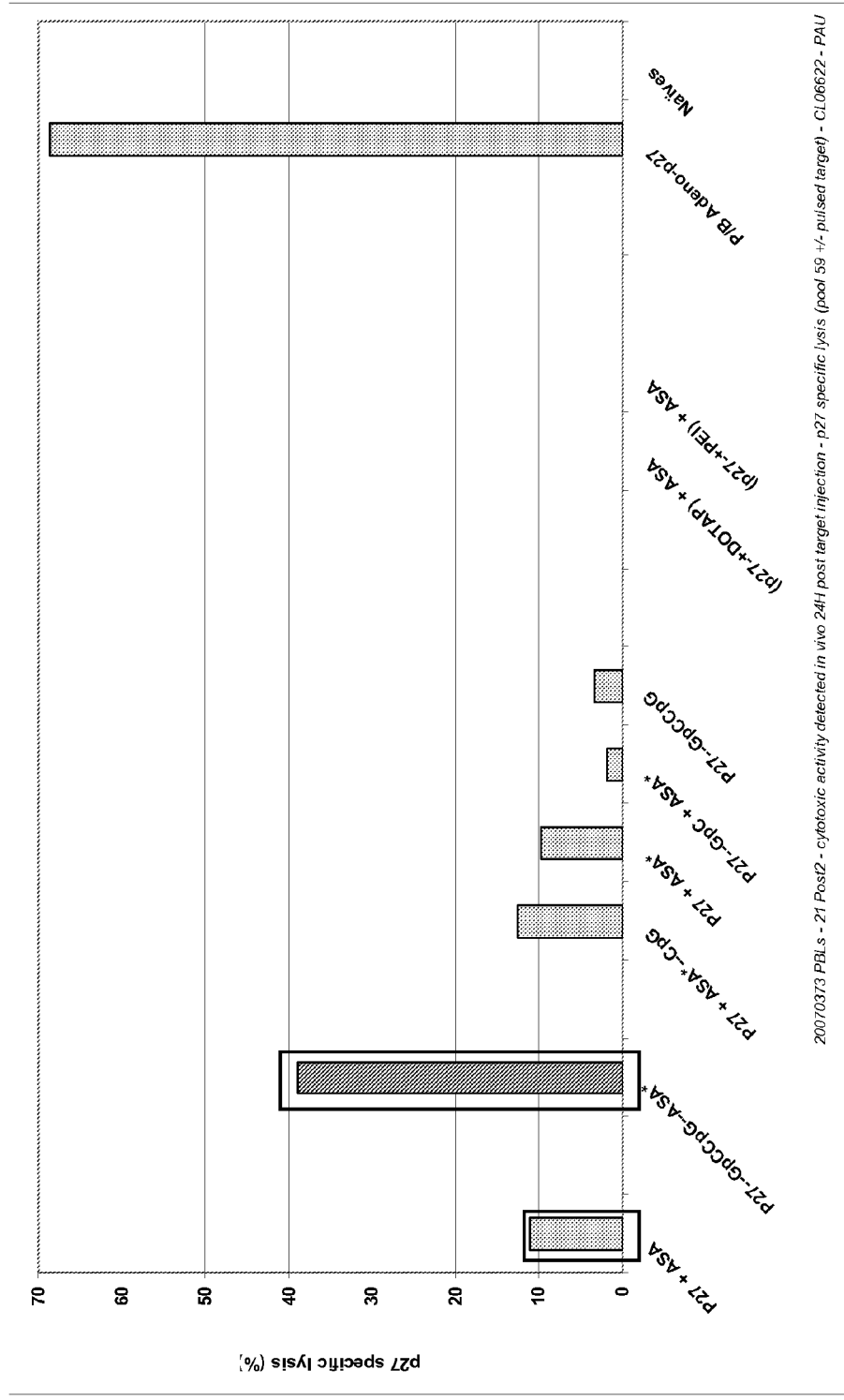
Figure 7 - Cell-mediated cytotoxicity detected *in vivo*

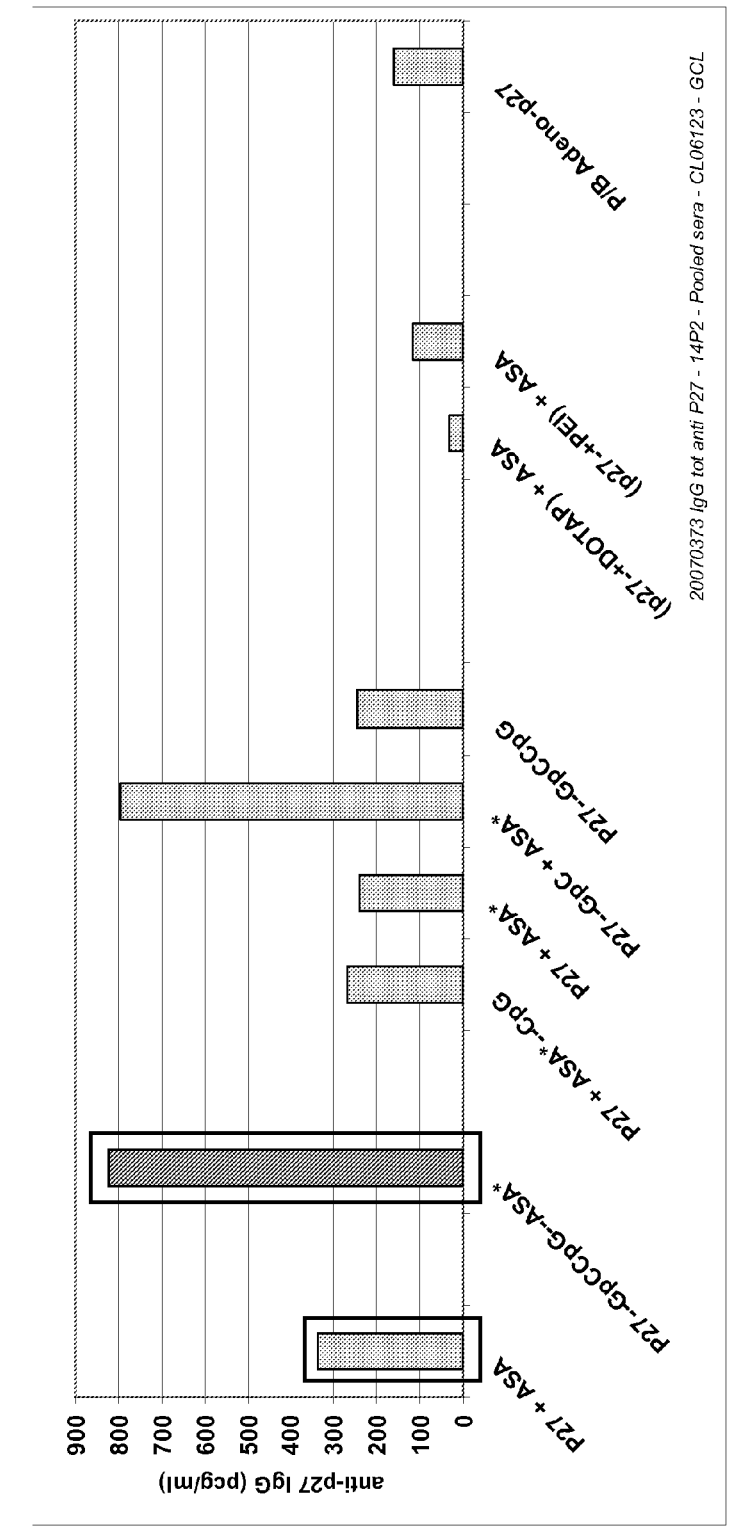
Figure 8- Anti-p27 antibody titre (total IgG – pooled sera)

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tccatgacgt tcctgacgtt                                               20

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
tctcccagcg tgcgccat                                                 18

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3
accgatgacg tcgccggtga cggcaccacg                                    30

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
tcgtcgtttt gtcgttttgt cgtt                                          24

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
tccatgacgt tcctgatgct                                               20

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide

<400> SEQUENCE: 6
tcgacgtttt cggcgcgcgc cg                                            22

<210> SEQ ID NO 7
<211> LENGTH: 24
<212> TYPE: DNA
<213> ORGANISM: Artificial Sequence

```
<220> FEATURE:
<223> OTHER INFORMATION: Oligonucleotide

<400> SEQUENCE: 7
ggtgtgtgca ttgcttggtg gtgg                                            24
```

US 8,846,080 B2

VACCINE

CROSS-REFERENCE TO RELATED APPLICATIONS

This application is filed pursuant to 35 USC 371 as a U.S. National Phase Application of International Patent Application Serial No. PCT/EP2009/060967 filed on Aug. 26, 2009, which claims the benefit of U.S. Provisional No. 61/092,582 filed Aug. 28, 2008, U.S. Provisional No. 61/095,747 filed Oct. 15, 2008 and U.S. Provisional No. 61/165,688 filed Apr. 1, 2009, which are incorporated herein in their entirety.

FIELD OF THE INVENTION

TECHNICAL FIELD

The present invention relates to vaccine and immunogenic compositions comprising particulate antigen delivery systems linked to antigens using intermediate linkers.

BACKGROUND OF THE INVENTION

New compositions or vaccines with an improved immunogenicity are always needed. As one strategy, adjuvants have been used to try and improve the immune response raised to any given antigen.

WO05/014110 discloses compositions which comprise a) a liposome b) at least one A-type CpG, wherein the A-type CpG is bound to or enclosed by the liposome. Shahum & Thérin [*Immunology* (1988) 65:315-317] disclose compositions comprising bovine serum albumin that is either free, encapsulated in liposomes or covalently linked to the liposomal surface using the hetero-bifunctional reagent N-Succinimidyl 3-(2-pyridyldithio)-propionate (SPDP). Using this method of classical conjugation the antigen is directly and covalently attached to the liposomes at an early stage of formulation. This attachment is not reversible unless enzymatically or chemically degraded. On the other hand, the encapsulation method is associated with a risk of denaturation and/or degradation of the antigen.

Alternative methods consist of the binding of antigens to ionically charged liposomes via electrostatic interactions. The HSV antigen gB was complexed to the cationic lipid DOTAP and successfully used to induce an immune response in vaccinated mice, in particular a CTL response (Walker et al. 1992-PNAS, 89: 7915-7918). HBsAg combined with the cationic lipid DC-chol generated an improved and balanced immunity able to overcome the unresponsiveness of mice to hepatitis B vaccine (Brunel at al. 1999.Vaccine 17: 2192-2203).

There is still a need for improved vaccine and immunogenic compositions that provide a suitable immune response.

SUMMARY OF THE INVENTION

The present inventors have demonstrated that vaccine or immunogenic compositions comprising particulate antigen delivery systems and antigen wherein the antigen and particles are linked using an intermediate linker, induce an immune response that is an improved immune response compared to compositions wherein the particles and antigen are not linked using an intermediate linker. In particular, the immunogenic compositions of the present invention induce an improved CD8+ T-cell immune response.

A particular embodiment of the invention provides an immunogenic composition comprising at least one antigen delivery particle and at least one antigen, wherein the antigen and antigen delivery particle are linked using an intermediate linker.

Particularly, in one embodiment of the invention there is provided an immunogenic composition wherein the linker comprises at least 2 components that are complementary to each other, wherein one of the linker components is linked to the antigen delivery particle and the complementary linker component is linked to an antigen; the antigen delivery particle and antigen are subsequently linked through hybridisation and/or joining of the complementary components to which they are attached.

In one embodiment of the invention, the linker is formed of complementary single stranded oligonucleotides. The oligonucleotide-mediated attachment allows for a reversible attachment with strength that can be adjusted by varying length and sequence of the oligonucleotides. This subsequently allows the antigen to be released after uptake by the cells. Moreover, the antigen is at the surface of antigen delivery particles with a linker of some length making it available for recognition by B-cells.

The present invention also allows a two vials concept, wherein the particulate antigen delivery systems and antigen can remain separate for packaging and transportation, for example, wherein they can be combined at an appropriate time point (possibly just before administration). The invention additionally allows the concept of generic particulate antigen delivery systems that can be combined to any antigen of interest. Moreover, by using different oligos that are attached to the particulate antigen delivery systems, one can attach different antigens (at different ratios if needed) to the same particle.

Accordingly, in the first aspect of the present invention there is provided an immunogenic composition comprising an antigen delivery particle and at least one antigen which are linked using an intermediate linker.

In one aspect of the invention there is provided an immunogenic composition comprising at least one antigen delivery particle and at least one antigen which are linked using an intermediate linker, wherein the linker comprises at least 2 components that are complementary to each other and wherein one of the linker components is linked to the particle and the other complementary linker component is linked to an antigen.

In a further aspect of the invention there is provided an immunogenic composition comprising at least one antigen delivery particle and at least one antigen which are linked using an intermediate linker, wherein the linker comprises at least 2 components that are complementary to each other and wherein one of the linker components is linked to the particle and the other complementary linker component is linked to an antigen, and wherein the 2 complementary linker components are hybridised.

In one aspect of the invention there is provided an immunogenic composition comprising at least one antigen delivery particle and at least one antigen which are linked using an intermediate linker, wherein said intermediate linker comprises at least one pair of complementary oligonucleotides.

In a further aspect of the invention there is provided the use of a vaccine or immunogenic composition comprising at least one antigen delivery particle and at least one antigen which are linked using an intermediate linker, wherein said intermediate linker comprises at least one pair of complementary oligonucleotides in the manufacture of an immunogenic composition for the prevention of infection and/or disease.

In a further aspect of the invention there is provided the use of a vaccine or immunogenic composition herein described in the manufacture of an immunogenic composition for the prevention and/or treatment of infection and/or disease.

In a further aspect, there is provided a method or use of a vaccine or immunogenic composition as herein defined, for protection against infection or disease caused by a pathogen which is a variant of the pathogen from which the antigen in the immunogenic composition is derived.

In another embodiment, there is provided a method or use of a vaccine or immunogenic composition as herein defined for protection against infections or disease caused by a pathogen which comprises an antigen which is a variant of that antigen in the immunogenic composition.

In a further embodiment of the invention there is provided a method or use of an immunogenic composition as herein defined for raising an antigen specific CD8+ T-cell immune response comprising administration to a patient with an immunogenic composition of the invention.

In a further aspect of the invention, there is provided a method or use of a vaccine or immunogenic composition as herein defined for treatment of a disease in mammals.

In a further aspect of the invention there is provided a kit comprising i) at least one antigen delivery particle linked to an oligonucleotide and ii) at least one antigen linked to an oligonucleotide that is complementary to the oligonucleotide in i).

BRIEF DESCRIPTION OF FIGURES

FIG. 1: SDS-PAGE/Coomassie analysis of the different eluted fractions.

FIG. 2: SDS-PAG/BET analysis of the different eluted fractions.

FIGS. 3A and 3B: SDS-PAGE analysis of pellet and supernatant after ultracentrifugation of the hybridization reaction mixture.

FIG. 4: Study design.

FIG. 5: Cytokine producing CD8+ T-cells frequency (%) within CD8+ population).

FIG. 6: Cytokine producing CD4+ T-cells frequency (%) within CD4+ population).

FIG. 7: Cell-mediated cytotoxicity detected in vivo.

FIG. 8: Anti-p27 antibody titre (total IgG—pooled sera).

DETAILED DESCRIPTION OF THE INVENTION

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa.

The present inventors have demonstrated that vaccine or immunogenic compositions of the present invention as herein described elicit an improved immune response compared to compositions wherein the antigen delivery particle and antigen are not linked using an intermediate linker. By 'improved immune response', it is meant that the immune response is modified in one or more of the following ways: increased number of effector cells (e.g. CD8+ and/or CD4+ T-cells, B-cells); increased effectiveness of one or more of the effector cell types; increased production of one or more cytokines by one or more cell types; and increased production of one or more cytokines as a proportion of the total cytokine profile. In particular, the immunogenic compositions of the present invention induce an improved CD8+ T-cell immune response.

An improved CD8+ T-cell response is important for prevention and/or treatment of certain diseases wherein a target cell may be infected with an intra-cellular bacteria or virus, for example HIV, or the target cell may be a tumour cell.

Accordingly, in the first aspect of the present invention there is provided an immunogenic composition comprising at least one antigen delivery particle and at least one antigen which are linked using an intermediate linker.

A further advantage of using an intermediate linker with complementary components is that different bulks of particles/antigen can be readily associated with different antigen(s)/antigen delivery particle(s), respectively. This is a further advantage over direct covalent linkage.

Particularly, there is provided an immunogenic composition wherein the linker comprises at least 2 components that are complementary to each other, wherein one of the linker components is linked to an antigen delivery particle and the complementary linker component is linked to an antigen; the antigen delivery particle and antigen are subsequently linked through hybridisation and/or joining of the complementary components to which they are attached.

Accordingly, in a particular aspect of the invention there is provided an immunogenic composition comprising at least one antigen delivery particle and at least one antigen which are linked using an intermediate linker, wherein said intermediate linker comprises at least one pair of complementary oligonucleotides.

In a particular aspect of the invention the immunogenic compositions of the invention comprise an immunogenic composition comprising at least one antigen delivery particle and at least one antigen which are linked using an intermediate linker, wherein said intermediate linker comprises at least one pair of complementary oligonucleotides wherein a first oligonucleotide is linked to is linked to the antigen delivery particle and a second oligonucleotide that is complementary to the first is linked to an antigen.

In a further aspect of the invention there is provided an immunogenic composition comprising at least one antigen delivery particle linked to one or more antigens via one or more pairs of complementary oligonucleotides. In a further embodiment the immunogenic composition comprises at least one antigen delivery particle linked to one or more antigens; the antigens may all be the same or one or more of the antigens may be different. In a further embodiment of the invention there is provided an immunogenic composition comprising an antigen delivery particle composition, wherein one or more of the antigen delivery particles are different. In a further embodiment of the invention there is provided an immunogenic composition one or more different antigen delivery particles and 1 or more different antigens.

Particulate Antigen Delivery Systems.

Particulate delivery systems are well known in the art (see for example Singh and O'Hagan 2002 Pharmaceutical Research 19(6): 715-727) and include oil in water emulsions, microparticles (see O'Hagen & Singh 2003 *Expert Rev. Vaccines* 2(2): 269-283), immunostimulatory complexes (IS-COMs), proteosomes, oil droplets and liposomes. The term 'antigen delivery particle' as used herein refers to a single particle of a particulate antigen delivery system, which includes but not limited to, an oil droplet of an oil in water emulsion, a single microparticle or nanoparticle, a single proteosome, a single oil droplet, a single liposome, a micelle, proteosome, or a single ISCOM.

Liposomes

A particular embodiment of the invention relates to immunogenic compositions comprising a liposomal formulation, which is linked to an antigen using an intermediate linker.

In one aspect of the invention there is provided an immunogenic composition comprising at least one liposome and at least one antigen which are linked using an intermediate linker, wherein the linker comprises at least 2 components that are complementary to each other and wherein one of the linker components is linked to the liposome and the other complementary linker component is linked to an antigen.

In a further aspect of the invention there is provided an immunogenic composition comprising at least one liposome and at least one antigen which are linked using an intermediate linker, wherein the linker comprises at least 2 components that are complementary to each other and wherein one of the linker components is linked to the liposome and the other complementary linker component is linked to an antigen, and wherein the 2 complementary linker components are hybridised.

In particular embodiments of the invention the intermediate linker comprises at least one pair of complementary oligonucleotides.

The term "liposomes" generally refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Lipids, which are capable of forming liposomes include all substances having fatty or fat-like properties. Lipids which can make up the lipids in the liposomes can be selected from the group comprising of glycerides, glycerophospholipids, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids.

In one embodiment the liposomes comprise a phospholipid. Suitable phospholipids include (but are not limited to): phosphocholine (PC) which is an intermediate in the synthesis of phosphatidylcholine; natural phospholipid derivates: egg phosphocholine, egg phosphocholine, soy phosphocholine, hydrogenated soy phosphocholine, sphingomyelin as natural phospholipids; and synthetic phospholipid derivates: phosphocholine (didecanoyl-L-α-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine DSPE 1,2-Dioleoyl-sn-Glycero-3-Phosphoethanolamine [DOPE]), phoshoserine, polyethylene glycol [PEG] phospholipid (mPEG-phospholipid, polyglycerin-phospholipid, funcitionilized-phospholipid, terminal activated-phosholipid). In one embodiment the liposomes comprise 1-palmitoyl-2-oleoyl-glycero-3-phosphoethanolamine. In one embodiment highly purified phosphatidylcholine is used and can be selected from the group comprising Phosphatidylcholine (EGG), Phosphatidylcholine Hydrogenated (EGG) Phosphatidylcholine (SOY) Phosphatidylcholine Hydrogenated (SOY). In a further embodiment the liposomes comprise phosphatidylethanolamine [POPE] or a derivative thereof.

Liposome size may vary from 30 nm to several pm depending on the phospholipid composition and the method used for their preparation. In particular embodiments of the invention, the liposome size will be in the range of 50 nm to 500 nm and in further embodiments 50 nm to 200 nm. Dynamic laser light scattering is a method used to measure the size of liposomes well known to those skilled in the art.

In further embodiments of the invention, the liposomes of the invention are linked to more than one oligonucleotide, for example 1 to 10,000, 1 to 15,000, 1 to 25,000, 1 to 50,000, 1 to 90,000, 1 to 100,000, or more oligonucleotides. The oligonucleotides linked to the antigen may all be the same or one or more may be different.

In further embodiments liposomes of the invention further comprise a sterol. Suitable sterols include β-sitosterol, stigmasterol, ergosterol, ergocalciferol and cholesterol. In one particular embodiment, the liposome comprises cholesterol as the sterol. These sterols are well known in the art, for example cholesterol is disclosed in the Merck Index, 11th Edn., page 341, as a naturally occurring sterol found in animal fat.

Immunogenic compositions of the invention may comprise more than one type of liposome. Liposomes may differ in their composition and thus in one embodiment of the invention there is provided an immunogenic composition comprising one or more different liposomes. Liposomes may differ in that they consist or comprise different elements, comprise further elements, lack certain elements or that the one or more of the elements from which the liposomes are comprised is/are in different proportions. Liposomes can differ in their composition i.e. in the phospholipids from which they are derived. In further embodiments, liposomes may differ in the amount of sterol present in the liposome, for example in one embodiment the immunogenic composition comprises a proportion of liposomes that comprise sterol and a proportion that do not comprise a sterol, or liposomes may differ the amount of sterol. In a further embodiment, immunogenic compositions may comprise liposomes that differ in the immunostimulants that are present; for example, in one embodiment the immunogenic composition may comprise a proportion of liposomes that comprise an immunostimulant, such a saponin and/or a TLR ligand, and liposomes that lack additional immunostimulants. In a further embodiment there is provided an immunogenic composition that comprises liposomes that differ in the oligonucleotide to which that are linked. For example, immunogenic compositions of the invention can comprise a proportion of liposomes linked to a particular oligonucleotide or set of oligonucleotides, whereas the remaining liposomes can comprise alternative oligonucleotides or sets of oligonucleotides. Immunogenic compositions can comprise any number of different types of liposome, for example 1, 2, 3, 4, 5, 6, 7, 8, 9, 10, 20, 30 or more different liposomes. Of course some liposomes may not be linked to one or more oligonucleotides whilst others are linked to one more different types of oligonucleotide.

Oil in Water Emulsions

In an embodiment of the present invention there is provided an immunogenic composition of the invention comprising at least one oil droplet in an oil in water emulsion and at least one antigen which are linked using an intermediate linker.

In one aspect of the invention there is provided an immunogenic composition comprising at least one oil droplet in an oil in water emulsion and at least one antigen which are linked using an intermediate linker, wherein the linker comprises at least 2 components that are complementary to each other and wherein one of the linker components is linked to the oil droplet and the other complementary linker component is linked to an antigen.

In a further aspect of the invention there is provided an immunogenic composition comprising at least oil droplet in an oil in water emulsion and at least one antigen which are linked using an intermediate linker, wherein the linker comprises at least 2 components that are complementary to each other and wherein one of the linker components is linked to the oil droplet and the other complementary linker component is linked to an antigen, and wherein the 2 complementary linker components are hybridised.

In particular embodiments of the invention the intermediate linker comprises at least one pair of complementary oligonucleotides.

Oil in water emulsions of the present invention comprise a metabolisable oil and an emulsifying agent. In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others.

A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no. 8619). In a further embodiment of the invention, the metabolisable oil is present in the immunogenic composition in an amount of 0.5% to 10% (v/v) of the total volume of the composition.

The oil in water emulsion further comprises an emulsifying agent. The emulsifying agent may suitably be polyoxyethylene sorbitan monooleate. Further, said emulsifying agent is suitably present in the vaccine or immunogenic composition in an amount of 0.125 to 4% (v/v) of the total volume of the composition.

The oil in water emulsion of the present invention optionally comprise a tocol. Tocols are well known in the art and are described in EP0382271. Suitably may be a tocol is alpha-tocopherol or a derivative thereof such as alpha-tocopherol succinate (also known as vitamin E succinate). Said tocol is suitably present in the adjuvant composition in an amount 0.25% to 10% (v/v) of the total volume of the immunogenic composition.

The method of producing oil-in-water emulsions is well known to the person skilled in the art. Commonly, the method comprises mixing the oil phase (optionally comprising a tocol) with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

In particular, the oil-in-water emulsion systems of the present invention have a small oil droplet size in the sub-micron range. Suitably the droplet sizes will be in the range 120 to 750 nm, more particularly sizes from 120 to 600 nm in diameter. Even more particularly, the oil-in water emulsion contains oil droplets of which at least 70% by intensity are less than 500 nm in diameter, more particular at least 80% by intensity are less than 300 nm in diameter, more particular at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or preferably the Malvern Zetasizer 3000HS. A first possibility is to determine the z average diameter ZAD by dynamic light scattering (PCS-Photon correlation spectroscopy); this method additionally give the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

Immunogenic compositions of the invention may comprise more than one type of oil droplet. Oil droplets within an oil in water emulsion may differ in their composition and thus in one embodiment of the invention there is provided an immunogenic composition comprising one or more different oil droplets. Oil droplets may differ in that they consist or comprise different elements, comprise further elements, lack certain elements or that the one or more of the elements from which the oil droplets are comprised is/are in different proportions. Oil droplets can differ in their composition i.e. in the lipids from which they are derived. In a further embodiment there is provided an immunogenic composition that comprises oil droplets that differ in the oligonucleotide to which that are linked. For example, immunogenic compositions of the invention can comprise a proportion of oil droplets linked to a particular oligonucleotide or set of oligonucleotides, whereas the remaining liposomes can comprise alternative oligonucleotides or sets of oligonucleotides. Immunogenic compositions can comprise any number of different types of oil droplets, for example 1, 2, 3, 4, 5, 6, 7, 8, 9, 10, 20, 30 or more different oil droplets.

ISCOMs

In an embodiment of the present invention there is provided an immunogenic composition of the invention comprising at least one ISCOM and at least one antigen which are linked using an intermediate linker.

In one aspect of the invention there is provided an immunogenic composition comprising at least one ISCOM and at least one antigen which are linked using an intermediate linker, wherein the linker comprises at least 2 components that are complementary to each other and wherein one of the linker components is linked to the ISCOM and the other complementary linker component is linked to an antigen.

In a further aspect of the invention there is provided an immunogenic composition comprising at least ISCOM and at least one antigen which are linked using an intermediate linker, wherein the linker comprises at least 2 components that are complementary to each other and wherein one of the linker components is linked to the ISCOM and the other complementary linker component is linked to an antigen, and wherein the 2 complementary linker components are hybridised.

In particular embodiments of the invention the intermediate linker comprises at least one pair of complementary oligonucleotides.

ISCOMs are well known in the art (see Kersten & Crommelin [1995] *Biochimica et Biophysica Acta* 1241:117-138). ISCOMs comprise a saponin, cholesterol and phospholipids and from an open-cage-like structure of typically 40 nm in size. ISCOMs result from the interaction of saponins, cholesterol and further phospholipids. A typical reaction mixture for the preparation of ISCOM is 5 mg/ml saponin and 1 mg/ml each for cholesterol and phospholipid.

Phospholipids suitable for use in ISCOMs of the present invention include but are not limited to phosphocholine (didecanoyl-L-α-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine DSPE 1,2-Dioleoyl-sn-Glycero-3-Phosphoethanolamine [DOPE]), phoshoserine, polyethylene glycol [PEG] phospholipid (mPEG-phospholipid, polyglycerin-phospholipid, funcitionilized-phospholipid, terminal activated-phosholipid). In one embodiment of the invention ISCOMs comprise 1-palmitoyl-2-oleoyl-glycero-3-phosphoethanolamine. In a further embodiment highly purified phosphatidylcholine is used and can be selected from the group comprising Phosphatidylcholine (EGG), Phosphatidylcholine Hydrogenated (EGG) Phosphatidylcholine (SOY) Phosphatidylcholine Hydrogenated (SOY). In a further embodiment the ISCOMs comprise phosphatidylethanolamine [POPE] or a derivative thereof.

A number of saponins are suitable for use in ISCOMs of the present invention. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP 0 362 279 B1.

ISCOMs comprising fractions of Quil A have been used in the manufacture of vaccines (Morein, B., EP 0 109 942 B1). These structures have been reported to have adjuvant activity (EP 0 109 942 B1; WO 96/11711).

Fractions of QuilA, derivatives of QuilA and/or combinations thereof are suitable saponin preparations for use in ISCOMs of the present invention. The haemolytic saponins QS21 and QS17 (HPLC purified fractions of Quil A) have been described as potent adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711 and these are incorporated herein. Other particular QuilA fractions designated QH-A, QH-B, QH-C and a mixture of QH-A and QH-C designated QH-703 are disclosed in WO1996011711 in the form of ISCOMs and are incorporated herein.

Microparticles

In an embodiment of the present invention there is provided an immunogenic composition of the invention comprising at least one microparticle and at least one antigen which are linked using an intermediate linker.

Microparticles, compositions comprising microparticles, and methods of producing microparticles are well known in the art (see Singh et al. [2007 *Expert Rev. Vaccines* 6(5):797-808] and WO/1998/033487). The term "microparticle" as used herein, refers to a particle of about 1000 nm to about 150 μm in diameter, derived from polymeric materials which have a variety of molecular weights and, in the case of the copolymers such as PLG, a variety of lactide:glycolide ratios. In particular, the microparticles will be of a diameter that permits parenteral administration without occluding needles and capillaries. Microparticles are also known as microspheres. Microparticle size is readily determined by techniques well known in the art, such as photon correlation spectroscopy, laser diffractometry and/or scanning electron microscopy.

Microparticles for use herein will be formed from materials that are sterilizable, non-toxic and biodegradable. Such materials include, without limitation, poly(a-hydroxy acid), polyhydroxybutyric acid, polycaprolactone, polyorthoester, polyanhydride.

In particular, microparticles of the present invention are derived from a poly(u-hydroxy acid), in particular, from a poly(lactide) ("PLAII") or a copolymer of D,L-lactide and glycolide or glycolic acid, such as a poly(D,L-lactide-co-glycolide) ("PLGII or "PLGAII), or a copolymer of D,L-lactide and caprolactone.

Biodegradable polymers for manufacturing microparticles of the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly(ahydroxy acid), such as poly(L-lactide), poly(D,Llactide) (both known as "PLAII herein), poly(hydoxybutyrate), copolymers of D,L-lactide and glycolide, such as poly(D,L-lactide-co-glycolide) (designated as "PLG" or "PLGA" herein) or a copolymer of D,L-lactide and caprolactone. Particular polymers are PLA and PLG polymers. These polymers are available in a variety of molecular weights, and the appropriate molecular weight for a given antigen is readily determined by one of skill in the art. Thus, e.g., for PLA, a suitable molecular weight will be on the order of about 2000 to 5000. For PLG, suitable molecular weights will generally range from about 10,000 to about 200,000, particularly about 15,000 to about 150,000, and even more particularly about 50,000 to about 100,000. If a copolymer such as PLG is used to form the microparticles, a variety of lactide:glycolide ratios may be used.

Mixtures of microparticles with varying lactide:glycolide ratios will find use in the formulations in order to achieve the desired release kinetics for a given antigen and to provide for both a primary and secondary immune response. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837-858.

Nanoparticles

In an embodiment of the present invention there is provided an immunogenic composition of the invention comprising at least one nanoparticle and at least one antigen which are linked using an intermediate linker.

Nanoparticles are well known in the art. Compositions comprising nanoparticles and the preparation of nanoparticles are disclosed in WO/2008/051245 and Singh et al. (2007 *Expert Rev. Vaccines* 6(5):797-808) and incorporated herein by reference.

The term "nanoparticle" as used herein, refers to a particle of less than 1000 nm in diameter derived from polymeric materials. Nanoparticles have the same/similar compositions as those of microparticles (see above) and differ only in their size. Nanoparticles are also known as nanospheres. The nanoparticles within the compositions of the present invention typically have a size distribution in which the Z average and/or the D(v,0.5) value is less than 250 nm, and more typically less than 150 nm and in which the Z average and/or D(v,0.9) is less than 350 nm, and more typically less than 200 nm.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a particle that has the same translational diffusion coefficient as the particle. [0028] Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis. For static light scattering measurements (and also for photon correlation spectroscopy in some embodiments), volume-based size parameters may be measured.

For instance, the D(v,0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value. Similarly, the D(v,0.9) is a size parameter whose value is defined as the point where 90% (volume basis) of the particles in the composition have a size that is less than the D(v,0.9) value, and 10% of the particles in the composition have a size that is greater than the D(v,0.9) value.

Oligonucleotides

In a further embodiment of the invention there is provided a composition comprising at least one antigen delivery particle as herein described linked to at least one antigen using an intermediate linker, wherein said intermediate linker comprises at least one pair of complementary oligonucleotides.

The term oligonucleotide is well known in the art. The term "oligonucleotide" is used herein to mean any single-stranded oligonucleotide sequence. An oligonucleotide may be an RNA or DNA oligonucleotide or an oligonucleotide may be a peptide nucleic acid, or in an alternative embodiment may form a triple DNA helix. Thus, an 'oligonucleotide' according to the invention refers to a single-stranded oligonucleotide sequence that is capable of hybridising to a complementary nucleic acid. The design (length and specific sequence) of the oligonucleotide will depend on the nature of the antigen delivery particle and/or antigen, as well as on the conditions at which the oligonucleotide is used (such as temperature and ionic strength). The design of the oligonucleotide may depend upon the type of antigen delivery particle or antigen to be linked. The length of the oligonucleotide can determine the specificity and strength of the linkage and can be varied according to the distance desired between the antigen and liposome surface. The sequence of the oligonucleotide can be varied according to the desired immunostimulatory effect of the oligonucleotide. The oligonucleotide can be of any length and is limited only by its ability to hybridise and/or the ease by which it can be synthesised. In one embodiment the oligonucleotide are between 8 and 250 bases (for example 10 to 200, 12 to 75, 13 to 50, 10 to 45, 14 to 40), specifically the oligonucleotide may be 15, 16, 17, 18, 19, 20, 21, 22, 23, 24, 25, 26, 27, 28, 29, 30, 35, 40 bases in length.

The pairs of complementary oligonucleotides may be of any sequence provided they are suitable for binding to each other and capable of attachment to the either the liposome and/or antigen. In one embodiment the sequence of the first oligonucleotide sequences is that of any of SEQ ID NO: 1 to 6 or may be 10, 15, 20, 25, 30, 35, 40, 45, 50, 75, 100 or more bases which comprise or fall within the sequences of SEQ ID NO: 1 to 6. The second of the pair of oligonucleotides is complementary to the first. When needed, slight modifications to the length and/or sequence of the oligonucleotide may be carried out so as to maintain the specificity and sensitivity required under any given circumstance. Oligonucleotides listed herein may be extended by 1 to 40 or 1, 2, 3, 4, 5, 6, 7 8, 9 or 10 nucleotides, for example, in either direction.

In one embodiment of invention the oligonucleotides are immunostimulatory oligonucleotides. The term "immunostimulatory oligonucleotide" is used herein to mean an oligonucleotide that is capable of activating a component of the immune system. In one embodiment of the invention the immunostimulatory oligonucleotide comprises one or more unmethylated cytosine-guanosine (CpG) motifs. In a further embodiment, the immunostimulatory oligonucleotide comprises one or more unmethylated thymidine-guanosine (TG) motif or may be T-rich. By T-rich, it is meant that the nucleotide composition of the oligonucleotide comprises greater than 50, 60, 70 or 80% thymidine. In one embodiment of the invention the oligonucleotide is not an immunostimulatory oligonucleotide and does not comprise an unmethylated CpG motif. In a further embodiment the immunostimulatory oligonucleotide is not T-rich and/or does not comprise an unmethylated TG motif.

The oligonucleotide may be modified in order to improve in vitro and/or in vivo stability. For example, in one embodiment of the invention the oligonucleotides are modified so as to comprise a phosphorothioate backbone, i.e. internucleotide linkages. Other suitable modifications including diphosphorothioate, phosphoroamidate and methylphosphonate modifications as well as alternative internucleotide linkages to oligonucleotides are well known to those skilled in the art and are encompassed by the invention.

In a further embodiment the oligonucleotides can be modified so as to enable conjugation to either an antigen delivery particle and/or antigen. Methods of modifying oligonucleotides are well known to the skilled person. In one embodiment, there is provided an oligonucleotide modified so as to comprise a free sulfhydryl group (SH). In a particular embodiment there is provided an oligonucleotide comprising a free sulfhydryl group at its 3' end. By 'free sulfhydryl group' it is meant that the group is available for chemical conjugation.

In one embodiment of the invention there is provided immunogenic compositions of the invention, wherein the antigen delivery particles of the immunogenic composition are linked to one or more oligonucleotides. Oligonucleotides on a single antigen delivery particle may all be the same, or alternatively, one or more different oligonucleotides may be linked to a single antigen delivery particle. Oligonucleotides within an immunogenic composition may all be the same or in an a further embodiment, immunogenic compositions of the invention comprise one or more different oligonucleotides.

In a further embodiment of the invention there is provided an immunogenic composition comprising 2 or more antigen delivery particles wherein a proportion of delivery particles are linked to one type of oligonucleotide and wherein a proportion are linked to one or more different oligonucleotides.

In a further embodiment of the invention there is provided an immunogenic composition comprising antigen(s) linked to one or more different oligonucleotides i.e. antigens of the invention can be linked to any number of different oligonucleotides, for example 1, 2, 3, 4, 5, 6, or more different oligonucleotides sequences. In a further embodiment of the invention there is provided an immunogenic composition comprising 2 or more different antigens wherein one antigen is linked to one type of oligonucleotide and wherein the one or more different antigen (s) are linked to one or more different oligonucleotides.

In a further embodiment there is provided an immunogenic composition wherein the antigen is linked to one or more different oligonucleotides sequences. By this it meant that a single antigen molecule can be linked to one or more than one oligonucleotide of differing sequence, however, in an alternative embodiment of the invention antigens that are the same as each other within an antigen population are linked to different oligonucleotides.

Conjugation

An embodiment of the invention relates to immunogenic compositions wherein an antigen delivery particle is linked to antigen using an intermediate linker. In a particular embodiment the intermediate linker comprises at least one pair of complementary oligonucleotides. The oligonucleotides can be attached to the antigen and/or liposome by any method known to those skilled in the art.

In a particular embodiment of the invention there is provided an immunogenic composition of the invention as described herein, wherein an oligonucleotide is linked to at least one antigen delivery particle by chemical conjugation and wherein an oligonucleotide complementary to the oligonucleotide linked to at least one antigen delivery particle, is linked to at least one antigen by chemical conjugation.

Antigens can have one or more, for example 1 to 10, 1 to 15, 1 to 25, 1 to 50, 1 to 200, 2 to 100, for example 2, 3, 4, 5, 6, 7, 8, 9, 10, 11, 12, 13, 14, 15, 16, 17, 18, 19, 20 or more oligonucleotides linked by chemical conjugation. Oligonucleotides may be conjugated to the antigen using chemistry well known to those skilled in the art.

In one embodiment the antigen is conjugated to the oligonucleotide using a bifunctional linker (for example S-GMBS [N-(γ-maleimidobutyryloxy)sulfo succinimide ester]) to introduce a maleimide group to the protein to which a oligonucleotide with an additional sulfhydryl group is subsequently conjugated. Further suitable reagents for adding a maleimde group can be selected from the group consisting of N-[α-Maleimidoacetoxy]succinimide ester (AMAS), N-[β-Maleimidopropyloxy] succinimide ester (BMPS), N[∈-Maleimidocaproyloxy]succinimide ester (EMCS), N-[γ-Maleimidobutyryloxy]succinimide ester (GMBS), m-Maleimidobenzoyl-N-hydroxysuccinimide ester (MBS), succinimidyl-4-[N-maleimidomethyl]-cyclohexane-1-carboxy-[6-amidocaproate] (LC-SMOG), succinimidyl-4-[N-maleimidomethyl]-cyclohexane-1-carboxylate, (SMOG), Maleimido(polyethylene oxide)$_{2, 4, 6, 8 \text{ or } 12}$ N-hydroxysuccinimide ester (SM(PEG)$_{2, 4, 6, 8 \text{ or } 12}$), succinimidyl 4-[p-maleimidophenyl]butyrate (SMPB), succinimidyl 6-[β-maleimidopropionamido) hexanoate (SMPH), N-[∈-Maleimidocaproyloxy] sulfosuccinimide ester (Sulfo-EMCS), m-Maleimidobenzoyl-N-hydroxysulfo-succinimide ester (Sulfo-MBS), Sulfosuccinimidyl-4-[N-maleimidomethyl]-cyclohexane-1-carboxylate (Sulfo-SMCC), N-[γ-Maleimidobutyryloxy]sulfo-succinimide ester (Sulfo-GMBS) and Sulfosuccinimidyl 4-[p-maleimidophenyl]butyrate (Sulfo-SMPB) (Pierce; Bioconjugate techniques Greg T. Hermanson Academic Press 1996).

In a further embodiment wherein the protein comprises one or more free sulfhydyl groups, prior to maleimide activation the free sulfhydryl groups are blocked with for example N-Ethylmaleimide.

There a number of further chemistries available to the skilled person and thus in one embodiment, antigens that do comprise free sulfhydryl groups may be modified in order to transform free amino groups into sulfhydryl groups after DTT treatment using reagents such as N-succinimidyl 3-[2-pyridylthio]propionate (SPDP) for example. Other reagents can be selected from the group consisting of: succinimidyl 6-[3-(2-pyridylthio)propionamido]hexanoate LC-SPDP, 4-Succinimidyloxycarbonyl-methyl-α-[2-pyridyldithio] toluene (SMPT), LC-SMPT, Sulfosuccinimidyl 3-[2-pyridylthio]propionate (Sulfo-SPDP), Sulfoccinimidyloxy-carbonyl-methyl-α-[2-pyridyldithio]toluene Sufo-SMPT, Sulfosuccinimidyl 6-methyl-α-[2-pyridyldithio]toluamido hexanoate Sulfo-LC-SMPT, Sulfosuccinimidyl 6-[3'-2-pyridylthio]propionamido]hexanoate (Sulfo-LC-SDPD) and N-acetyl homocysteine thiolactone:

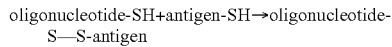

In an alternative embodiment an antigen comprising a sulfhydryl group can be modified using a bis-maleimide reagent, for example BM[PEO]$_{2\,or\,3}$ or DTME resulting in a maleimide activated antigen suitable for conjugation to a sulfhydryl (thiol) modified oligonucleotide:

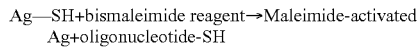

In an alternative embodiment a haloacetyl antigen maybe obtained by reaction with reagents such as SBAP, NHS-BA, SIA, SIAB and sulfo-SIAB. The resulting haloacetyl antigen may then be conjugated to a thiol-modified oligonucleotide:

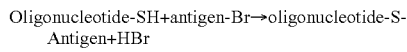

Liposomes may be linked to one or more, for example 1 to 100,000 oligonucleotides depending on the liposome size and other constraints such as steric hindrance of the oligonucleotides at the surface of liposomes. Oligonucleotides may be conjugated to the liposome using chemistry well known to those skilled in the art. Preparation of liposome conjugates and derivatives is well known (see Bioconjugate techniques. G T. Hermanson: preparation of liposome conjugates and derivatives pages 528-569 (1996)). Liposomes containing phosphatidyl ethanolamine groups can be activated using hetero-bifunctional cross-linkers to add maleimide, iodoacetyl or pyridyl disulfide groups.

Oligonucleotides can be linked any one of the components of a liposome, for example the phospholipid. In one embodiment the liposome comprises a maleimide modified phospholipid. In one embodiment the liposome comprises POPE-MAL (N-(3-maleimido-1-oxopropyl)L-α-phosphatidylethanolamine, 1-palmitoyl-2-oleyl [NOF American corporation] to which a thiol-modified oligonucleotide may be conjugated, for example.

Liposomes can be prepared to contain the modified phospholipids at a percentage ranging from 0.5% to 50% (molar). Particularly, the percentage of modified phospholipid is between 1 and 20% and even more particularly between 1 and 10%. The fraction of the modified phospholipid that will covalently attach to the oligonucleotides depends on the experimental conditions and yield of reaction.

Oligonucleotides can be linked any one of the components of an ISCOM, for example the phospholipid. In one embodiment the ISCOM comprises a maleimide modified phospholipid. In one embodiment the ISCOM comprises POPE-MAL to which a thiol-modified oligonucleotide may be conjugated, for example.

ISCOMs can be prepared to contain the modified phospholipids. The fraction of the modified phospholipid that will covalently attach to the oligonucleotides depends on the experimental conditions and yield of reaction. In a further embodiment the ISCOMS of the invention comprise modified cholesterol.

Oligonucleotides can be conjugated to oil droplets in oil in water emulsions. The oil droplets of oil in water emulsions of the invention may comprise a modified surfactant that is capable of conjugation to one or more an oligonucleotides. In one embodiment, there is provided oil droplets of the invention comprising a modified surfactant, wherein the surfactant is a modified phospholipid as herein defined. In a particular embodiment of the invention, the modified phospholipids is between about 0.1 and 10% (v/v) of the total surfactant volume.

Oligonucleotides can be conjugated to micro and/or nanoparticles. The micro/nanoparticles of the invention may comprise modified phospholipids that are capable of conjugation to one or more an oligonucleotides. In one embodiment, there is provided micro/nano particles of the invention comprising modified phospholipids as herein defined.

One embodiment of the invention there is provided a process for the manufacture of an immunogenic composition comprising the following steps:
a. Conjugating of a first oligonucleotide to an antigen;
b. Conjugating of a second oligonucleotide complementary to the oligonucleotide in step a) to an antigen delivery particle;
c. Mixing of the antigen and antigen delivery particle under conditions that allow hybridization of oligonucleotides.

In a further embodiment there is provided a process for the manufacture of an immunogenic composition comprising the steps:
a. Blocking of any free sulfhydryl groups on an antigen using a suitable reagent;
b. Adding a maleimide group to said antigen;
c. Conjugating a first thiol-activated oligonucleotide to said antigen;
d. Conjugating a second thiol oligonucleotide complementary to the oligonucleotide in step c) to a liposome comprising a maleimide-activated phospholipid;
e. Mixing of the antigen and liposome under conditions that allow hybridization of the oligonucleotides.

In a further embodiment there is provided a process for the manufacture of an immunogenic composition comprising the following steps:
a. Blocking of any free sulfhydryl groups on an antigen using a suitable reagent;
b. Adding a maleimide group to said antigen;
c. Conjugating a first thiol-activated oligonucleotide to said antigen;
d. Conjugating a second thiol oligonucleotide complementary to the oligonucleotide in step c) to a ISCOM comprising a maleimide-activated phospholipid;
e. Mixing of the antigen and ISCOM under conditions that allow hybridization of the oligonucleotides.

In a further embodiment there is provided a process for the manufacture of an immunogenic composition comprising the following steps:
a. Blocking of any free sulfhydryl groups on an antigen using a suitable reagent;
b. Adding a maleimide group to said antigen;
c. Conjugating a first thiol-activated oligonucleotide to said antigen;
d. Conjugating a second thiol oligonucleotide complementary to the oligonucleotide in step c) to a oil droplet comprising a maleimide-activated phospholipid;
e. Mixing of the antigen and oil droplet under conditions that allow hybridization of the oligonucleotides.

In a further embodiment there is provided a process for the manufacture of an immunogenic composition comprising the following steps:
a. Blocking of any free sulfhydryl groups on an antigen using a suitable reagent;
b. Adding a maleimide group to said antigen;
c. Conjugating a first thiol-activated oligonucleotide to said antigen;

d. Conjugating a second thiol oligonucleotide complementary to the oligonucleotide in step c) to a microparticle and/or nanoparticle comprising a maleimide-activated phospholipid;

e. Mixing of the antigen and microparticle and/or nanoparticle under conditions that allow hybridization of the oligonucleotides.

In a particular embodiment of the invention, there is provided a process for the manufacture an immunogenic composition as described herein wherein step b) is performed using a bi-functional linker/antigen molar ratio of approximately 6.

Antigens

The vaccine or immunogenic compositions of the invention will comprise an antigen capable of eliciting an immune response against a human or animal pathogen and/or a substance that causes pathogenesis in humans or animals. In a further embodiment of the invention, the vaccine or immunogenic compositions of the invention will comprise an antigen capable of eliciting an immune response against a tumour and/or tumour antigen or neoplasia in a human or animal.

The term 'antigen' is well known to the skilled person. An antigen can be a protein, polysaccharide, peptide, nucleic acid, protein-polysaccharide conjugates, molecule or hapten that is capable of raising an immune response in a human or animal. Antigens may be derived, homologous or synthesised to mimic molecules from viruses, bacteria, parasites, protozoan or fungus. In an alternative embodiment of the invention the antigen derived, homologous or synthesised to mimic molecules from a tumour cell or neoplasia. In a further embodiment of the invention the antigen is derived, homologous or synthesised to mimic molecules from a substance implicated in allergy, Alzheimer's disease, atherosclerosis, obesity and nicotine-dependence.

In one embodiment of the invention there is provided an immunogenic composition comprising one or more antigen delivery particles wherein the antigen delivery particle(s) is/are linked to 1 or more antigens via an intermediate linker. In a further embodiment of the invention there is provided an immunogenic composition comprising one or more antigen delivery particles, wherein the antigen delivery particles are linked to 1 or more antigens via a linker and wherein the linker comprises at least one pair of complementary oligonucleotides. The antigen delivery particles of the invention are linked to any number of antigens, for example 1 to 200,000 antigen molecules; this is dependent upon the particular antigen delivery particle. The antigens may all be the same or in an alternative embodiment there may be one or more different antigens and thus the antigen delivery particles of the invention may be linked to any number of different antigens, for example 1, 2, 3, 4, 5, 6, 7, 8, 9, 10, 20, 30, 40, 50, 60 or more different antigens.

In a further embodiment of the invention, the antigen is linked to more than one oligonucleotide, for example 1 to 200, 2 to 100, 1 to 50, 1 to 25, 1 to15, 1 to 10, for example 2, 3, 4, 5, 6, 7, 8, 9, 10, 11, 12, 13, 14, 15, 16, 17, 18, 19, 20 or more oligonucleotides. The oligonucleotides linked to the antigen can be all the same or alternatively, one or more of the oligonucleotides may be different to each other.

Immunogenic compositions of the invention comprise antigen delivery particle linked to linker components and antigens linked to complementary linker components. Suitably, at least 30% or more the antigen molecules are linked to antigen delivery particles in the composition. In further embodiments of the invention at least about 40% or more of the antigen molecules are linked to antigen delivery particles. In further embodiments of the invention a majority of the antigen is linked to antigen delivery particles, that is to say over 50% of the antigen molecules in the composition are linked to antigen delivery particles. In a further embodiment of the invention substantially all of the antigen molecules in the composition are linked to antigen delivery particles of the composition. By substantially all is meant that at least at least 60%, 70%, 80%, 90%, 95% or more of the antigen molecules are linked to antigen delivery particles. In one embodiment of the invention, all (approximately 100%) of the antigen present in the immunogenic compositions of the invention is linked to antigen delivery particles in the composition. Any excess unbound antigen molecules can be removed from the compositions by a variety of methods known to the person skilled in the art, for example, the immunogenic compositions may be subjected to centrifugation wherein the antigen linked to antigen delivery particles is pelleted and the antigen that is not linked to liposomes remains in the supernatant.

Kit

An advantage of the invention is the ease with which oligonucleotide linked antigens can then be linked to antigen delivery particles linked to complementary oligonucleotides. Within the scope of the invention are kits comprising antigen delivery particles and antigens linked to complementary linker components. In a particular embodiment, there is provided kits comprising antigen delivery particles and antigens linked to complementary oligonucleotides. The antigen delivery particles and antigens conjugated to complementary oligonucleotides within the kits of the invention may be hybridised to each other or can be separate, thus requiring hybridisation prior to administration to the host.

In a certain aspect of the invention there is provided a kit, wherein the kit comprises i) at least one antigen delivery particle linked to one or more oligonucleotides. In a further aspect of the invention there is provided a kit, wherein the kit comprises i) at least one antigen linked to one or more oligonucleotides.

In one embodiment of the invention there is provided a kit, wherein the kit comprises i) at least one antigen delivery particle linked to one or more oligonucleotides and ii) at least one antigen linked to one or more oligonucleotides that are complementary to the oligonucleotides in i). In a further embodiment of the invention, there is provided a kit that comprises i) at least one antigen delivery particle linked to one or more oligonucleotides and ii) 2 or more different antigens linked to one or more oligonucleotides that are complementary to the oligonucleotides in i). In a further embodiment of the invention, there is provided a kit that comprises i) one or more antigen delivery particles linked to an oligonucleotide ii) one or more different types of antigen delivery particle linked to either oligonucleotides of i) or different oligonucleotides; and iii) one or more antigens that are linked to one or more oligonucleotides that are complementary to the oligonucleotides to i) and/or ii); and optionally iv) one or more different antigens that are linked to oligonucleotides that are complementary to the oligonucleotides of i) and/or ii).

In one embodiment of the invention there is a provided a kit wherein at least one antigen delivery particle is linked to at least one antigen via hybridisation via the complementary oligonucleotides or the at least one antigen is linked to at least one antigen delivery particle via hybridisation via the complementary oligonucleotides.

In an alternative embodiment of the invention there is provided a kit wherein the antigen delivery particle (s) and antigen (s) are in different vials and thus not hybridised via complementary oligonucleotides so that they can be hybridised at an appropriate time point before administration.

Kits can comprise any number of different types of antigen delivery particle for example, ranging from 1 to 100 different types of antigen delivery particle. In one embodiment, one type of antigen delivery particle is linked to identical oligonucleotides, in an alternative embodiment each different type of antigen delivery particle can be linked to different oligonucleotides. In a further embodiment kits of the invention can comprise any number of different antigens, for example 1 to 100 different antigens. Antigens in the kit are suitably linked to oligonucleotides that are complementary to oligonucleotides that are linked to at least one set of liposomes within the kit.

In a further embodiment there is provided a kit that comprises i) at least one antigen delivery particle linked to one or more oligonucleotides and ii) at least one antigen linked to one or more oligonucleotides that are complementary to the oligonucleotides; and iii) a further immunostimulant.

Immunostimulants

In a further embodiment of the invention there is provided a vaccine or immunogenic composition as substantially described herein further comprising at least one immunostimulant or combinations of immunostimulants.

In one embodiment of the invention there is provided an immunogenic composition comprising at least one antigen delivery particle and at least one antigen are linked using an intermediate linker, wherein said intermediate linker comprising at least one pair of complementary oligonucleotides, further comprising one or more immunostimulants. Immunostimulants can be within the liposome (either in the lipid bilayer or encapsulated in the internal aqueous phase), ISCOM or droplet, ad mixed with the antigen delivery particle in an aqueous solution, or in a further embodiment the components of the composition may be adsorbed to the additional immunostimulant.

The optional immunostimulant is selected from the group: a saponin, lipid A or a derivative thereof, an immunostimulatory oligonucleotide, an alkyl glucosaminide phosphate, a metal salt, a toll-like receptor agonist or combinations thereof. In a particular embodiment the immunostimulant/adjuvant is a Toll like receptor agonist in particular an agonist of a Toll like receptor 2, 3, 4, 7, 8 or 9, or a saponin. Particular combinations contain a saponin (in particular QS21) adjuvant and/or a Toll like receptor 4 agonist such as 3D-MPL or a Toll like receptor 9 agonist such as a CpG containing immunostimulatory oligonucleotide. Other combinations comprise a saponin (in particular QS21) and a Toll like receptor 4 agonist such as a saponin (in particular QS21) and a Toll like receptor 4 ligand such as 3D-MPL or an alkyl glucosaminide phosphate.

In an embodiment the immunostimulant is a Toll like receptor (TLR) 4 ligand, particularly an agonist such as a lipid A derivative particularly monophosphoryl lipid A or more particularly 3 Deacylated monophoshoryl lipid A (3 D-MPL). 3D-MPL is sold under the name MPL by GlaxoSmithKline Biologicals N.A. and is referred throughout the document as MPL or 3D-MPL. see, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. In particular embodiments, small particle 3D-MPL is used in the compositions of the present invention. Small particle 3D-MPL has a particle size such that it may be sterile-filtered through a 0.2 µm filter. Such preparations are described in WO 94/21292.

The immunogenic compositions may further comprise an immunostimulant which is a lipopolysaccharide, suitably a non-toxic derivative of lipid A, particularly monophosphoryl lipid A or more particularly 3-Deacylated monophoshoryl lipid A (3D—MPL). In one embodiment of the invention the immunogenic compositions comprise 3D-MPL.

Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol 1,10-bis(dihydrogenophosphate) (WO99/64301 and WO 00/0462)

OM 197 MP-Ac DP (3S-,9R) -3-[(R)-dodecanoyloxytetradecanoylamino]-4-oxo-5-aza-9-[(R)-3-hydroxytetradecanoylamino]decan-1,10-diol 1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as immunostimulants.

Other suitable TLR-4 ligands, capable of causing a signalling response through TLR-4 (Sabroe et al, JI 2003 p 1630-5) are, for example, lipopolysaccharide from gram-negative bacteria and its derivatives, or fragments thereof, in particular a non-toxic derivative of LPS (such as 3D-MPL). Other suitable TLR agonist are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP) or F protein of respiratory syncitial virus. In one embodiment the TLR agonist is HSP 60, 70 or 90.

Toll-like receptors (TLRs) are type I transmembrane receptors, evolutionarily conserved between insects and humans. Ten TLRs have so far been established (TLRs 1 to 10) (Sabroe et al, JI 2003 p 1630-5). Members of the TLR family have similar extracellular and intracellular domains; their extracellular domains have been shown to have leucine—rich repeating sequences, and their intracellular domains are similar to the intracellular region of the interleukin—1 receptor (IL-1R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also posses the IL-1R domain in its cytoplasmic region, leading to NF-KB activation of cytokines; this Myd88 pathway is one way by which cytokine release is effected by TLR activation. The main expression of TLRs is in cell types such as antigen presenting cells (eg dendritic cells, macrophages etc).

Activation of dendritic cells by stimulation through the TLRs leads to maturation of dendritic cells, and production of inflammatory cytokines such as IL-12. Research carried out so far has found that TLRs recognise different types of agonists, although some agonists are common to several TLRs. TLR agonists are predominantly derived from bacteria or viruses, and include molecules such as flagellin or bacterial lipopolysaccharide (LPS).

By "TLR agonist" it is meant a component which is capable of causing a signalling response through a TLR signalling pathway, either as a direct ligand or indirectly through generation of endogenous or exogenous ligand (Sabroe et al, JI 2003 p 1630-5).

In another embodiment, other natural or synthetic agonists of TLR molecules are used as optional immunostimulants. These could include, but are not limited to agonists for TLR2, TLR3, TLR7, TLR8 and TLR9.

In one embodiment of the present invention, a TLR agonist is used that is capable of causing a signalling response through TLR-1 (Sabroe et al, JI 2003 p 1630-5). Suitably, the TLR agonist capable of causing a signalling response through TLR-1 is selected from: Tri-acylated lipopeptides (LPs); phenol-soluble modulin; Mycobacterium tuberculosis LP; S-(2, 3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorfei*.

In an alternative embodiment, a TLR agonist is used that is capable of causing a signalling response through TLR-2 (Sabroe et al, JI 2003 p 1630-5). Suitably, the TLR agonist capable of causing a signalling response through TLR-2 is one or more of a lipoprotein, a peptidoglycan, a bacterial lipopeptide from *M. tuberculosis, B. burgdorferi, T. pallidum*; peptidoglycans from species including *Staphylococcus aureus*; lipoteichoic acids, mannuronic acids, *Neisseria porins*, bacterial fimbriae, *Yersinia* virulence factors, CMV virions, measles haemagglutinin, and zymosan from yeast.

In an alternative embodiment, a TLR agonist is used that is capable of causing a signalling response through TLR-3 (Sabroe et al, JI 2003 p 1630-5). Suitably, the TLR agonist capable of causing a signalling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signalling response through TLR-5 (Sabroe et al, JI 2003 p 1630-5). Suitably, the TLR agonist capable of causing a signalling response through TLR-5 is bacterial flagellin.

In an alternative embodiment, a TLR agonist is used that is capable of causing a signalling response through TLR-6 (Sabroe et al, JI 2003 p 1630-5). Suitably, the TLR agonist capable of causing a signalling response through TLR-6 is mycobacterial lipoprotein, di-acylated LP, and phenol-soluble modulin. Further TLR6 agonists are described in WO2003043572.

In an alternative embodiment, a TLR agonist is used that is capable of causing a signalling response through TLR-7 (Sabroe et al, JI 2003 p 1630-5). Suitably, the TLR agonist capable of causing a signalling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO02085905.

In an alternative embodiment, a TLR agonist is used that is capable of causing a signalling response through TLR-8 (Sabroe et al, JI 2003 p 1630-5). Suitably, the TLR agonist capable of causing a signalling response through TLR-8 is a single stranded RNA (ssRNA), an imidazoquinoline molecule with anti-viral activity, for example resiquimod (R848); resiquimod is also capable of recognition by TLR-7. Other TLR-8 agonists which may be used include those described in WO2004071459.

Immunostimulatory oligonucleotides or any other Toll-like receptor (TLR) 9 agonist may also be used (in addition to those used in hybridization). Particular oligonucleotides for use in vaccines or immunogenic compositions of the present invention are CpG containing oligonucleotides, in particular containing two or more dinucleotide CpG motifs separated by at least three, even more particularly at least six or more nucleotides. A CpG motif is a Cytosine nucleotide followed by a Guanine nucleotide. The CpG oligonucleotides of the present invention are typically deoxynucleotides. In a particular embodiment the internucleotide in the oligonucleotide is phosphorodithioate, or a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, 5,278,302 and WO95/26204.

Examples of particular oligonucleotides for use in the present invention have the following sequences. In particular embodiments of then invention, the sequences contain phosphorothioate modified internucleotide linkages.

```
(SEQ ID NO 1):
TCC ATG ACG TTC CTG ACG TT (CpG 1826)

(SEQ ID NO 2):
TCT CCC AGC GTG CGC CAT (CpG 1758)

(SEQ ID NO 3):
ACC GAT GAC GTC GCC GGT GAC GGC ACC ACG (SEQ ID NO 4):
TCG TCG TTT TGT CGT TTT GTC GTT (CpG 2006)

(SEQ ID NO 5):
TCC ATG ACG TTC CTG ATG CT (CpG 1668)

(SEQ ID NO 6):
TCG ACG TTT TCG GCG CGC GCC G (CpG 5456)
```

Alternative CpG oligonucleotides may comprise the sequences above in that they have inconsequential deletions or additions thereto. The CpG oligonucleotides utilised in the present invention may be synthesized by any method known in the art (for example see EP 468520). Conveniently, such oligonucleotides may be synthesized utilising an automated synthesizer.

Accordingly, in another embodiment, the compositions of the invention further comprise an immunostimulant selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment of the invention, the immunogenic composition further comprises a saponin. A particularly suitable saponin for use in the present invention is Quil A and its derivatives. Quil A is a saponin preparation isolated from the South American tree *Quillaja Saponaria Molina* and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a particular saponin in the context of the present invention.

The saponin adjuvant within the immunogenic compositions of the invention in particular are immunologically active fractions of Quil A, such as QS-7 or QS-21, suitably QS-21. In one embodiment the compositions of the invention contain the immunologically active saponin fraction in substantially pure form. In particular, the compositions of the invention contain QS21 in substantially pure form, that is to say, the QS21 is at least 75%, 80%, 85%, 90% pure, for example at least 95% pure, or at least 98% pure.

In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In one embodiment the liposomes of the invention that comprise a saponin suitably contain a neutral lipid, for example phosphatidylcholine, which is suitably non-crystalline at room temperature, for example eggyolk phosphatidylcholine, dioleoyl phosphatidylcholine (DOPC) or dilauryl phosphatidylcholine. The liposomes may also contain a charged lipid which increases the stability of the liposome-QS21 structure for liposomes composed of saturated lipids. In these cases the amount of charged lipid is suitably 1 to 20% w/w, particularly 5 to 10%. The ratio of sterol to phospholipid is 1 to 50% (mol/mol), suitably 20 to 25%.

Immunogenic compositions of the invention comprising QS21 and a sterol, cholesterol in particular, show a decreased reactogenicity when compared to compositions in which the sterol is absent, while the adjuvant effect is maintained. Reactogenicity studies may be assessed according to the methods disclosed in WO 96/33739. The sterol according to the invention is taken to mean an exogenous sterol, i.e. a sterol which is not endogenous to the organism from which the antigenic preparation is taken but is added to the antigen preparation or subsequently at the moment of formulation.

Where the active saponin fraction is QS21, the ratio of QS21: sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

Other useful saponins are derived from the plants *Aesculus hippocastanum* or *Gyophilla struthium*. Other saponins which have been described in the literature include Escin, which has been described in the Merck index (12$^{th}$ ed: entry 3737) as a mixture of saponins occuring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). Sapoalbin from *Gypsophilla struthium* (R. Vochten et al., 1968, J. Pharm. Belg., 42, 213-226) has also been described in relation to ISCOM production for example.

In a particular, compositions may comprise two or more immunostimulants from the above list. In one embodiment the immunogenic compositions of the invention comprise both lipopolysaccharide and immunologically active saponin. In a further embodiment of the invention, the lipopolysaccharide is incorporated into liposomes of the invention. In a specific embodiment of the invention, the lipopolysaccharide is 3D-MPL and the immunologically active saponin is QS21 are incorporated into liposomes of the invention.

Vaccination

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times. In addition, the vaccines of the invention may be administered IM for priming doses and IN for booster doses.

The content of protein antigens in the vaccine will typically be in the range 1-500 µg, preferably 5-350 µg, most typically in the range 5 - 300 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The amount of each antigen in each vaccine dose is selected as an amount which induces an immunoprotective response without significant, adverse side effects in typical vaccinees. Such amount will vary depending upon which specific immunogen is employed and how it is presented.

In a further embodiment there is provided a method of treatment of an individual susceptible to or suffering from a disease by the administration of a composition as substantially described herein.

Also provided is a method to prevent an individual from contracting a disease selected from the group comprising infectious bacterial and viral diseases, parasitic diseases, particularly intracellular pathogenic disease, proliferative diseases such as prostate, breast, colorectal, lung, pancreatic, renal, ovarian or melanoma cancers; non-cancer chronic disorders, allergy comprising the administration of a composition as substantially described herein to said individual.

In a further embodiment there is provided a vaccine composition for use in the prophylactic therapy or therapy of a condition or disease wherein the vaccine composition comprises at least one liposome and at least one antigen in the form of a complex, wherein the antigen and liposome are linked using an intermediate linker.

In a further embodiment there is provided the use of a vaccine in the manufacture of a medicament for use in prophylactic therapy or therapy of a condition or disease wherein the vaccine comprises a composition as substantially described herein.

The invention will be further described by reference to the following, non-limiting, examples:

EXAMPLES

I—Formulation of Liposomes Linked to Antigen Via an Intermediate Linker

I.1. Conjugation of the p27 antigen to the GpC—SH single strand ODN (deoxyoligonucleotide).
Method:
I.1.1. Blocking the —SH Function of the Ag Using N-Ethylmaleimide (NEM)

The p27 antigen contains an intrinsic —SH capable of reacting with maleimides. In order to avoid a premature reaction of this SH with maleimide, it was chemically blocked.

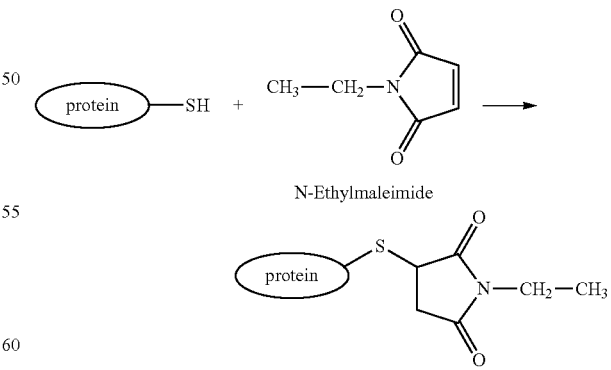

Accordingly, P27 (SIV) was incubated with a 25-fold molar excess of N-Ethylmaleimide (Sigma, MW 125.12) at room temperature under agitation during 1 hour. Excess reagent was removed on a PD10 column (Amersham) using 100 mM phosphate pH 6.8 as elution buffer. Fractions of 1 ml were collected and monitored by absorbance at 280 nm. Those containing NEM modified p27 were pooled and analysed by Lowry (protein content). Efficacy of the reaction was estimated by Ellman's dosage.

Fractions 2-4, containing the purified antigen, were collected and pooled.

A direct Ellman assay was performed on the pooled fraction to verify that all SH functions were blocked.

I.1.2. Activation of p27

8.7 ml of SH-blocked p27 (NEM modified p27) at ~1.1 mg/ml was incubated for 1 h (RT, magnetic sterring) (N-[γ-maleimidobutyryloxy]sulfo-succinimide ester, Pierce) at a S-GMBS/p27 molar ratio of 6. By-products and excess of reagent were removed using a PD10 column (Amersham) and 100 mM phosphate pH 6.8 as elution buffer. Fractions of 1 ml were collected and monitored by absorbance at 280 nm. Fractions containing maleimide-activated p27 were pooled. Protein content was estimated by Lowry. The number of maleimide functions on p27 was estimated by an indirect Ellman's dosage (2.4 maleimide functions detected). The S-GMBS N-(gamma-maleimidobutyryloxy-succinimide ester) is a bifunctional reagent containing a succinimide function on one side and a maleimide on the other. Succinimide react with —NH functions (e.g. of the alkaline amino-acids of a protein) and maleimide react with sulfhydryl groups (—SH).

Quantification of p27 in the pool using the Lowry assay revealed 1.33 mg/ml (for a total volume of 5.6 ml). An indirect Ellman assay was applied to verify the activation yield. The data showed that the S-GMBS/p27 ratio of 6 resulted in activation of an average of 2 functions per protein. Gel electrophoresis showed that this ratio gave a relatively homogenous activated p27 population. Using higher ratios (7.5 and 15) resulted in a smear pattern of higher molecular weight bands suggesting that cross-linking of several proteins may have occurred (data not shown). Hence the 6 molar ratio was selected for further experiments.

1.1.3. Conjugation of p27 Antigen and GpC—SH ODN

Maleimide-activated p27 was incubated with a 3.6-fold molar excess of GpC—SH (available from Eurogentec, 1.5-fold excess molar by comparison with the number of maleimide functions; a phosphodiester oligonucleotide of the sequence complementary to that shown in SEQ ID NO: 4 with a thiol group at the 3' end) in a phosphate buffer at pH 6.8. After 1 h at room temperature, Cysteine (Merck, 4 mg/ml) was added to quench the reaction i.e. the non reacting maleimides functions were then neutralized using excess cysteine. GpC excess was removed by dialysis against 2 mM phosphate buffer 150 mM NaCl pH 6.8. However, analysis by SDS-PAGE shows that as free protein and free GpC are still present in the conjugate, this one was purified by gel filtration (Superdex 75). Elution was done in 2 mM phosphate 150 mM NaCl pH 6.8. Fractions of 1 ml were collected and monitored by absorbance at 260 and 280 nm. Fractions containing only the conjugate were pooled.

FIG. 1 (Coomassie blue staining) shows that fractions 21-23 contain p27-GpC conjugates, fractions 24, 25 contain mixtures of unconjugated p27 and p27-GpC conjugates where as the other fractions contain only unconjugated p27. FIG. 2 (Ethidium bromide or BET staining) shows that free GpC appear at fractions 24-29.

Fractions 24-26 were then submitted to a second purification step using the Superdex 75 column. The fractions containing only conjugates were then pooled and mixed with fractions 21-23. The final pool was analysed by SDS-PAGE and Coomassie staining. A 42 kDa band was observed on the gel indicating that, on average, two GpC oligo were linked to each p27 protein.

The conjugate was stored at −20° C. until use.

I. 2. Conjugation of Liposomes to the Complementary CpG-SH Oligo

In order to covalently attach the CpG-SH oligo (a phosphodiester CpG of the sequence as shown in SEQ ID NO:4 with a thiol group at the 3' end) onto the surface of liposomes, modified liposomes incorporating a POPE-MAL lipid derivative (POPE with a maleimide function attached at its polar head group), were prepared. The used method (lipid film hydration) is described hereunder.

DOPC (8.7 mg), Cholesterol (2.5 mg), 3D-MPL (0.5 mg) and POPE-MAL [N-(3-maleimido-1-oxopropyl)L-α-phosphatidylethanolamine, 1-palmitoyl-2-oleyl, NOF American corporation] (1.3 mg representing ~10% mole of DOPC were solubilized in 2 ml chloroform. The chloroform was subsequently evaporated under nitrogen flow and dried under

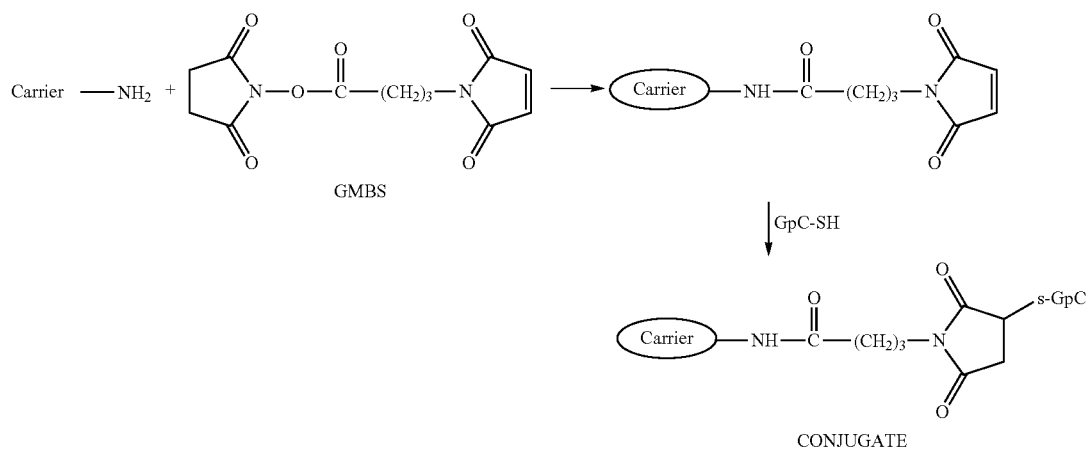

vacuum during 3 h. The dry lipid film was added with 1 ml of 10 mM PO4-150 mM NaCl, pH 7.2 containing 7.5 mg of CpG-SH (representing 1.5-fold molar excess of CpG-SH over POPE-MAL).

The so-formed lipid film was then vortexed in hydration medium until complete resuspension of the lipidic film. The presence of CpG-SH in the hydration medium allowed for the reaction between SH and maleimide to occur before degradation of the rather unstable maleimide functions. The solution was sonicated using a probe sonicator (50 W) for 2 min to obtain SUV (single unilamellar vesicle) then incubated 1h at 40° C. under magnetic stirring.

At the end of incubation, CpG-incorporating liposomes were purified from free CpG-SH by ultracentrifugation (200,000 g, 1 h at 4° C.). The supernatant (containing free CpG) was removed and the pellet (containing liposome-CpG) was resuspended in 100 µl of buffer.

As a final step, the unreacted maleimide functions at the surface of liposomes were quenched using cysteine (25 molar excess) at RT for 30 min. The liposomes were again pelleted to remove excess cysteine and resuspended in 100 µl buffer.

Pellet and supernatant from the two ultracentrifigations were analyzed by 3% agarose gel electrophoresis and staining with ethidium bromide to detect presence of CpG (data not shown).

I. 3. Hybridization of Liposomes and p27.

In order to allow for GpC conjugated p27 association onto the liposome, a hybridization step was typically performed as follows. To this end 1.5 ml of liposome-CpG conjugate (15 mg/ml DOPC) and 3 ml of p27-GpC conjugate (0.5 mg/ml p27) were mixed in PBS buffer, pH 7.4 and incubated for 30 min at 37° C. As a control to ensure specific binding of p27-GpC on the liposome-CpG via DNA hybridization, p27-GpC was incubated in parallel with liposomes lacking CpG oligo at their surface.

Both test and control were then ultracentrifuged to allow for separation between p27-bound liposomes (pellet) and free p27-GpC (supernatant). Pellet and supernatants were then analysed by SDS-PAGE and Coomassie staining. The data for two representative experiments are shown in FIGS. 3A and 3B. The majority of the p27 was detected in the pellet in the case of the test but not the control indicating that the presence of CpG oligo at the surface of liposomes allowed an efficient association of p27 to the liposomes.

QS21 was added to immunogenic composition to a concentration of 100 ug following hybridisation. This formulation will be denoted "P27--GpCCpG--ASA*" as explained in table 1 and annexed box.

Of note, for immunization experiments, the mixture resulting from hybridization was injected without removal of the p27-GpC that was not associated.

In Vivo Testing of Liposomes Linked to Antigen by Oligonucleotide Linkers

Materials and Methods
Reagents and Medium

Formulations summarized and described below were used to vaccinate 6 -8 week old C57BL/B6 (H2Kb), female mice (10/group). The mice received two injections spaced 14 days apart and were bled during weeks 4, 5 and 6 (for actual bleed days see FIG. 4). The mice were vaccinated intramuscularly (injection into the left gastrocnemius muscle of a final volume of 50 µl) with ex-tempo formulation. A heterologous prime boost using recombinant adenovirus coding for the SIV-p27 protein and adjuvanted p27 was used as control group, the adenovirus was injected at a dose of $5\times10^8$ VP. The study design is represented in FIG. 4.

Summary of Formulations Tested in Vivo

The following table (Table 1) summarizes all tested formulations including control formulations. Compositions of the invention are highlighted.

TABLE 1

Summary of tested formulations.

| | | p27 | Liposome | MPL | QS21 |
|---|---|---|---|---|---|
| Formulation content | Quantity | Antigen association | Lipid Composition | Quantity | |
| P27 + ASA | 5 µg | Ad-mixed with liposomes | DOPC/Chol | 5 µg | 5 µg |
| P27--GpCCpG--ASA* | 5 µg | Substantially all linked to liposomes using a linker | DOPC/Chol/POPE/MAL | 5 µg | 5 µg |
| P27 + ASA*--CpG | 5 µg | Ad-mixed with liposomes | DOPC/Chol/POPE/MAL | 5 µg | 5 µg |
| P27 + ASA* | 5 µg | Ad-mixed with liposomes | DOPC/Chol/POPE/MAL | 5 µg | 5 µg |
| P27--GpC + ASA* | p27-GpC 5 µg | Ad-mixed with liposomes | DOPC/Chol/POPE/MAL | 5 µg | 5 µg |
| P27--GpCCpG | p27-GpCCpG 5 µg | N/A | N/A | — | — |
| (p27- + DOTAP) + ASA | 5 µg | Ionically bound to DOTAP liposomes | (DOTAP/DOPE) & DOPC/Chol | 5 µg | 5 µg |
| (p27- + PEI) + ASA | 5 µg | Ionically bound to polymers | DOPC/Chol | 5 µg | 5 µg |

+: components before and after the sign were ad-mixed (no association was used).
--: components before and after the sign were covalently attached.
--GpCCpG--: means that the component before the sign was linked to the component after the sign using oligo hybridisation (a linker).
ASA*: 10% of POPE-MAL included in the liposome bilayer of ASA.
P27- + DOTAP: p27 was ionically bound to the liposomes.
P27- + PEI: p27 was ionically bound to the polymers.

For clarification of the adjuvant antigen combination strategy used, and in particular, the design of control groups, a legend is provided below to enable the skilled person to easily determine the content of each formulation and link the description in the text with the figures. The legend clarifies formulations referred to in Table 1 (above), the text and the Figures below.

II—1.1 Preparation of Control Formulations.
II—1.1.1 ASA-containing Formulations.

A mixture of lipid (such as phosphatidylcholine either from egg-yolk or synthetic) and cholesterol and 3 D-MPL in organic solvent, was dried down under vacuum (or alternatively under a stream of inert gas). An aqueous solution (such as phosphate buffered saline) was then added, and the vessel agitated until all the lipid was in suspension. This suspension was then microfluidised until the liposome size was reduced to about 100 nm, and then sterile filtered through a 0.2 µm filter. Typically the cholesterol:phosphatidylcholine ratio was 1:4 (w/w), and the aqueous solution was added to give a final cholesterol concentration of 5 to 50 mg/ml. The liposomes have a defined size of 100 nm and are referred to as SUV (for small unilamelar vesicles). QS21 in aqueous solution was added to the SUV. PBS composition was $Na_2HPO_4$: 8.1 mM; $KH_2PO_4$: 1.47 mM; KCl: 2.7 mM; NaCl: 137 mM pH 7.4. This mixture is referred as ASA. The ASA was diluted in the presence of the p27 antigen so that p27, 3 D-MPL and QS21 were all at a final concentration of 100 µg/ml. This formulation is denoted "p27+ASA".

II—1.1.2. Association of p27 to DOTAP-containing Liposomes or PEI (Polyethyleneimine) Polymer.

To prepare DOTAP-containing liposomes, DOTAP (N-[1-(2,3-Dioleoyloxy)propyl]-N,N,Ntrimethylammonium methylsulfate) and DOPE (dioleoylphosphatidylethanolamine) at a molar ratio of 1/1 were mixed in chloroform and the solvent evaporated under a stream of nitrogen to obtain a lipid film. The film was hydrated with a buffer containing 50 mM Hepes and 6% sucrose pH 7.4 to reach a DOTAP final concentration of 20 mg/ml. The obtained vesicles were sequentially extruded through polycarbonate membranes of 400 nm then 100 nm.

To prepare p27/DOTAP-DOPE complex, 2 ml of p27 at 200 µg/ml were mixed with 2 ml of DOTAP/DOPE liposomes at 4 mg/ml DOTAP concentration and the mixture allowed to incubate at RT for 30 min. The buffer composition of this mixture was Hepes: 5 mM; sucrose: 9%; pH 7.4. To estimate the association efficiency, liposomes were pelleted by ultracentrifugation at 200,000 g and p27 was assayed in the pellet and supernatant using a modified Lowry procedure. The association yield in this experiment was estimated to approximately 60-70% of p27 bound to liposomes. This formulation is denoted "p27-+DOTAP".

PEI (MW=750 KD) was solubilized in 50 mM Hepes+6% sucrose at pH 6.8. To prepare p27/PEI complex, 2 ml of p27 at 200 µg/ml in 50 mM Hepes, 6% sucrose, pH 6.8 were mixed with 2 ml of PEI at 4 mg/ml in 50 mM Hepes, 6% sucrose pH 6.8 and the mixture allowed to incubate at RT for 30 min. This formulation is denoted "p27-+PEI".

The ASA adjuvant was admixed to these two formulations prior to administration into mice so that the ASA concentration was equivalent to that used for other groups.

II—1.2 Organ Collection
II—1.2.1 PBLs Isolation

Blood was taken from retro orbital vein (50 µl per mouse, 10 mice per group) and directly diluted in RPMI+heparin (LEO) medium. PBLs were isolated through a lymphoprep gradient (CEDERLANE). Cells were then washed, counted and finally were re-suspended at ad hoc dilution in a ad hoc buffer (see below).

II—1.2.2 Spleen Cell Isolation

Briefly, total cells were extracted by disruption of spleen, cells are then re-suspended within a large volume of RPMI (5 spleen within 35 ml). Spleen cells are isolated through a lymphoprep gradient (CEDERLANE). Lymphocytes are then washed, counted and finally re-suspended at ad hoc dilution in ad hoc buffer for their further used as target cells in the CMC assay.

II—1.2.3 Lymph Node Cell Isolation

Briefly, total cells are extracted by disruption of the draining lymph nodes. These cells are carefully washed twice, counted and finally re-suspended at ad hoc dilution in ad hoc buffer for their further used as target cells in the CMC assay.

II—1.3 Immunological Assays
II—1.3.1 Intracellular cytokine Staining (ICS).

ICS was performed on blood samples taken as described above. This assay includes two steps: ex vivo stimulation and staining. Ex vivo lymphocyte stimulation is performed in complete medium which is RPMI 1640 (Biowitaker) supplemented with 5% FCS (Harlan, Holland), 1 µg/ml of each anti-mouse antibodies CD49d and CD28 (BD, Biosciences), 2 mM L-glutamine, 1 mM sodium pyruvate, 10 µg/ml streptamycin sulfate, 10 units/ml penicillin G sodium (Gibco), 10 µg/ml streptamycin 50 µM B-ME mercaptoethanol and 100× diluted non-essential amino-acids, all these additives are from Gibco Life technologies. Peptide stimulations were always performed at 37° C., 5% $CO_2$.

STEP 1: Ex Vivo Stimulation (SIV-p27 Model)

For ex vivo stimulation, 5 to 10 $10^5$ PBLs were re-suspended in complete medium supplemented with a pool of 59 15-mer SIV-p27 peptides (each overlapping by 11 amino acids and encompassing different MHC class I-restricted peptides and MHC class II-restricted peptides purchased from Neosystem) present at a concentration of 1 µg/ml for each. After 2 hours, 1 µg/ml Brefeldin-A (BD, Biosciences) was added for 16 hours and cells were collected after a total of 18 hours.

STEP 2: Staining

Directly after stimulation, PBLs are stained. Briefly cells were washed once and then stained with anti-mouse antibodies all purchased at BD, Biosciences; all further steps were performed on ice. The cells were first incubated for 10 min. in 50 µl of CD16/32 solution (1/50 f.c., FACS buffer). 50 µl of T cell surface marker mix was added (1/100 CD8a perCp, 1/100 CD4 APC Cy7) and the cells were incubated for 20 min. before being washed. Cells were fixed & permeabilised in 200 µl of perm/fix solution (BD, Biosciences), washed once in perm/wash buffer (BD, Biosciences) before being stained at 4° C. with anti IFNg-APC, anti-TNFa-PE and anti IL2-FITC either for 2 hours or overnight. Data were analysed using a FACS Calibur™ with CELLQuest™ software, 15000 events within the gate of living CD8 are acquired per test.

II—1.3.2 Cell Mediated Cytotoxic Activity Detected in Vivo (CMC in Vivo)

To assess antigen-specific cytotoxicity in vivo, immunized and control mice were injected with a mixture of antigen specific and non-specific targets (ratio 1/1). Syngenic splenocytes and lymph node cells are loaded or not with 1 µg/ml of a pool of 59 15-mers peptide encompassing the whole SIV-p27 protein and then they are respectively labelled with a low and a high dose of CFSE. For the differential labeling, carboxyfluorescein succinimidyl ester (CFSE; Molecular Probes—Palmoski et al.; 2002, J. Immunol. 168, 4391-4398) was used at a concentration of 0.2 µM or 2.5 µM. Both types of targets were pooled at 1/1 ratio and re-suspended at a concentration of $10^8$ targets/ml. 200 µl of target mix were injected per mouse into the tail vein 21 days after $2^{nd}$ injection. Cytotoxicity was assessed by $FACS^R$ analysis on blood (jugular vein) taken from sacrificed animal 24 H after target injection. The mean percentage lysis of p27 specific target cells was calculated relative to antigen-negative controls with the following formula:

$$\text{lysis \%} = 100 - \left( \frac{\text{corrected target } (+)}{\text{control target } (-)} \times 100 \right)$$

$$\text{Corrected target } (+) = \text{target } (+) \times \frac{(preinj.-)}{(preinj.+)}$$

Pre-injected target cells=mix of peptide-pulsed targets (preinj.+) and non-pulsed (preinj.−) targets acquired by FACS before injection in vivo.

Corrected target (+)=number of peptide-pulsed targets acquired by FACS after injection in vivo, corrected in order to take into account the number of preinj+ cells in the preinjected mix (see above).

II—1.3.3 Antigen Specific Antibody Titer: (Pooled) Sera Analysis of Specific IgG (ELISA).

Serological analysis was assessed 2 weeks after second injection. Mice (10 mice per group) were bled by retro-orbital puncture.

Plate that are used are 96 well-plates (NUNC, Immunosorbant plates), their coating is different according to the antigen model.

For the SIV-p27 model: anti-SIV-p27 total IgG was measured by ELISA. 96 well-plates were coated with antigen overnight at 4° C. (100 µl per well of SIV-p27 solution 5 µg/ml in PBS). Revelation step was made as follow: plates were then washed in wash buffer (PBS/0.1% Tween 20 (Merck)) and saturated with 200 µl of saturation buffer (PBS/0.1% Tween 20/1% BSA) for 1 hour at 37° C. Saturation buffer was removed and 100 µl of diluted mouse serum was added and incubated for another 60 minutes at 37° C. After three washes, the plates were incubated for one hour at 37° C. with 100 µl of biotinylated anti-mouse total IgG diluted 1000 times in saturation buffer. After incubation 96 w plates were washed again as described above. A solution of streptavidin peroxydase (Amersham) diluted 1000 times in saturation buffer was added (100 µl per well). The last wash was a 5 steps wash in wash buffer. Finally, 100 µl OPDA (37.5 µl ml Citrate de Na–0.05% tween–pH4.5+15 mg OPDA+37.5 µl H2O2 added extempo) per well was added and the plate were kept in the dark at room temperature for 20 minutes. To stop the reaction, 100 µl of H2SO4 2N was added per well. The absorbance was read at a wavelength of 490/630 nm by an Elisa plate reader from BIORAD. Results were calculated using the Softmax-pro software.

II—2 Results

II—2.1 Cytokine Producing T-Cell Detected Ex Vivo (ICS)

FIG. 5 illustrates the cytokine producing CD8+ T-cell frequency detected for the different groups 7 days after second injection.

Primary CD8 response was very low (data not shown). Secondary responses reported in FIG. 8 are then the results of a clear boost of the primary response. 7 days post 2, CD8 frequency was very low for mice that have received the formulation containing free p27 and ASA (P27 + ASA). When p27 was bound to the surface of liposomes through DNA hybridization (P27--GpCCpG-ASA*), the CD8 response was clearly increased as compared to P27 + ASA, showing that the binding of p27 on the liposome had a clear enhancing impact on CD8+ T-cell response. Control formulations where antigen/liposome association via oligo hybridization was not possible were the followings: the formulation comprising POPE-MAL-containing liposome but without bound CpG (p27 + ASA*), or the formulation containing liposome associated to CpG but unmodified p27 (p27+ASA*--CpG), or the formulation with GpC conjugated to p27 but with liposome lacking CpG at their surface (p27--GpC+ASA*). All these control formulations induced a very low CD8 response (<0.5%). This indicated that the improvement of the CD8 response clearly required the association of the p27 to liposome via hybridization and was neither due to the chemical modifications of the antigen and/or liposomes, nor the sole presence of the modified CpG bound to the liposome. In conclusion, the overall data show that an improved CD8 response can be achieved by binding, via hybridization of complementary oligonucleotides, the antigen to the liposome containing the immunostimulants MPL and QS21. None of the mice injected with formulation containing cationic-lipid ((p27-+DOTAP) with ASA) or cationic polymer ((p27-+PEI) with ASA) induced detectable frequencies of p27-specific CD8+T-cell. These latter data indicate that association of antigen to particulate systems such as DOTAP liposomes or PEI polymer, via ionic interactions, is not sufficient to induce CD8 and hence suggest that improved CD8 response observed when antigen was associated to ASA via oligonucleotide hybridization was not simply due to particulation of the antigen.

FIG. 6 illustrates the cytokine producing CD4+ T-cell frequency detected for the different groups 7 days after second injection. As observed for the CD8 response, primary CD4 response was very low (data not shown). Responses reported in FIG. 9 are then the result of a clear boost of the immune response. At 7 days post 2, for the data clearly show that the association of the antigen to the liposome via hybridization has also a positive impact on the CD4 response (compare p27+ASA and P27--GpCCpG+ASA*.) As for the CD8 response, control formulations showed that the enhancement of the CD4 response was not due to the modification of the protein (p27-GpC+ASA*) or to the sole modification of the liposome (P27+ASA*) or the sole presence of CpG bound to the liposome (P27+ASA*-CpG). None of the mice injected with formulations containing cationic-lipid ((p27-+DOTAP) with ASA) or cationic polymer ((p27-+PEI) with ASA) induced detectable frequencies of p27 specific CD4+ T-cells.

II—2.2 Cytotoxic Activity Detected in Vivo (CMC)

FIG. 7 illustrates the cytotoxic activity detected in vivo 21 days after second injection. PBLs were analysed 24 H after injection target cells (for details, see materials and methods). The formulation in which p27 was bound to the surface of liposomes through DNA hybridization (P27--GpCCpG+ASA*) induced higher cytotoxic activity than the formulation containing free p27 and ASA (p27+ASA). None of the control groups (p27-GpC+ASA*, P27+ASA*, P27+ASA*-CpG) induced a level of cytotoxicity as high as the one induced by the P27--GpCCpG-ASA* formulation. None of the mice injected with formulation containing antigen associated with cationic-lipid ((p27-+DOTAP) with ASA), or cationic polymer ((p27-+PEI) with ASA) induced detectable cytotoxic activity in vivo.

II—2.3 Antigen Specific Antibody Titer: (Pooled) Sera Analysis of Specific IgG (ELISA).

FIG. 8 illustrates the anti-p27 IgG titer detected in individual sera collected 14 days after the second injection. P27-specific antibody titres are increased upon antigen association to liposomes via DNA hybridization. The formulation containing modified p27 and ASA (P27-GpC+ASA*) was here able to improve the antibody response. None of the groups injected with formulation containing cationic-lipid ((p27-+DOTAP) with ASA) or cationic polymer ((p27-+PEI) with ASA) induced higher antibody titres than that observed in mice receiving p27+ ASA.

Immunogenic compositions comprising oligonucleotides lacking CpG motifs (SEQ ID NO: 7 GGTGTGTGCATTGCTTGGTGGTGG and its complementary sequence) were also tested. For sample where hybridisation had been demonstrated there was a trend showing an increased immune response over non-hybridised controls although this was not statistically significant.

The invention claimed is:

1. An immunogenic composition comprising at least one antigen delivery particle and at least one antigen, wherein the antigen and antigen delivery particle are linked using an intermediate linker, wherein said intermediate linker comprises at least one pair of complementary oligonucleotide sequences, wherein a first oligonucleotide is linked to the antigen delivery particle and a second oligonucleotide that is complementary to the first is linked to an antigen and wherein the antigen is linked to the antigen delivery particles through hybridisation of complementary oligonucleotides.

2. The immunogenic composition of claim 1 wherein the antigen delivery particle is selected from the group consisting of: liposome, ISCOM, oil droplet within an oil in water emulsion, microparticle, nanoparticle, or oil droplet.

3. The immunogenic composition of claim 1 wherein the oligonucleotides are selected from the group: DNA, RNA, and PNA.

4. The immunogenic composition of claim 3 wherein the oligonucleotides are DNA.

5. The immunogenic composition of claim 1 wherein the oligonucleotides comprises a phosphorothioate backbone.

6. The immunogenic composition of claim 4 wherein at least one of the oligonucleotides comprises one or more CpG motifs.

7. The immunogenic composition of claim 4 wherein at least one the oligonucleotides does not comprise one or more CpG motifs.

8. The immunogenic composition of claim 6 wherein the oligonucleotide sequence comprising one or more CpG motifs comprises the sequence of SEQ ID NO: 4 (ODN 2006).

9. The immunogenic composition of claim 1 wherein the one or more oligonucleotides is modified so as to facilitate conjugation of said oligonucleotide to an antigen delivery particle and/or antigen.

10. The immunogenic composition of claim 9 wherein the one or more oligonucleotides is modified by the addition of a thiol (SH) group.

11. The immunogenic composition of claim 10 wherein the thiol group is conjugated to the 3' terminus of the oligonucleotide.

12. The immunogenic composition of claim 1 wherein at least one antigen delivery particle is linked to a first oligonucleotide by chemical conjugation.

13. The immunogenic composition claim 12 wherein at least one antigen is linked to a second oligonucleotide that is complementary to the first by chemical conjugation.

14. The immunogenic composition of claim 13 wherein at least one antigen is linked to at least one of the oligonucleotides by maleimide-based chemical conjugation.

15. The immunogenic composition of claim 1 wherein the immunogenic composition comprises an immunostimulant.

16. The immunogenic composition of claim 15 wherein the antigen delivery particle is a liposome and wherein at least one liposome comprises one or more immunostimulants.

17. The immunogenic composition of claim 15 wherein the immunostimulant is selected from the group consisting of: saponin; Toll-like Receptor 4 (TLR4) ligand; Toll-like receptor 7 and/or 8 (TLR7/8) ligand; Toll-like receptor 9 (TLR9) ligand; or any combination thereof.

18. The immunogenic composition of claim 16 wherein the liposome comprises a saponin and a TLR4 ligand.

19. The immunogenic composition of claim 17 wherein the saponin is a derivative of Quil A.

20. The immunogenic composition of claim 19 wherein the Quil A derivative is QS21.

21. The immunogenic composition of claim 17 wherein the TLR4 ligand is mono-phosphoryl lipid A.

22. The immunogenic composition of claim 1 wherein the antigen delivery particle is a liposome and wherein at least one liposome comprises a sterol.

23. The immunogenic composition of claim 22 wherein the sterol is cholesterol.

24. The immunogenic composition of claim 1 comprising one or more different antigens.

25. A process for making an immunogenic composition comprising the steps of:
   a. Conjugating of a first oligonucleotide to an antigen;
   b. Conjugating of a second oligonucleotide complementary to the oligonucleotide in step a) to an antigen delivery particle;
   c. Mixing of the antigen and antigen delivery particle under conditions that allow hybridization of the oligonucleotides.

26. A kit comprising i) at least one antigen delivery particle linked to an oligonucleotide and ii) at least one antigen linked to an oligonucleotide that is complementary to the oligonucleotide in i).

27. The kit according to claim 26 comprising one or more different types of antigen delivery particle.

28. The kit of either claim 26 or 27 comprising one or more different antigens.

29. The kit of claim 26 comprising one or more different oligonucleotides.

30. The kit of claim 26 claim further comprising one or more immunostimulants.

31. The kit of claim 26 wherein the at least one antigen delivery particle is linked to at least one antigen via hybridisation via the complementary oligonucleotides or the at least one antigen is linked to at least one antigen delivery particle via hybridisation via the complementary oligonucleotides.

32. The kit of claim 26 wherein the antigen delivery particle(s) and antigen(s) are not hybridised via complementary oligonucleotides.

* * * * *